(12) United States Patent
Ryu et al.

(10) Patent No.: US 10,991,069 B2
(45) Date of Patent: Apr. 27, 2021

(54) METHOD AND APPARATUS FOR REGISTRATION OF MEDICAL IMAGES

(71) Applicant: SAMSUNG ELECTRONICS CO., LTD., Suwon-si (KR)

(72) Inventors: Jiwon Ryu, Suwon-si (KR); Won-Chul Bang, Seongnam-si (KR); YoungTaek Oh, Seoul (KR); Kyong Joon Lee, Seongnam-si (KR); Min Woo Lee, Seoul (KR); Jungwoo Chang, Seoul (KR); Jayeon Jeong, Yongin-si (KR); Dong Kuk Shin, Guri-si (KR); Sung-Jin Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/878,020

(22) Filed: Oct. 8, 2015

(65) Prior Publication Data
US 2016/0104287 A1 Apr. 14, 2016

(30) Foreign Application Priority Data

Oct. 8, 2014 (KR) .................. 10-2014-0136091
Oct. 6, 2015 (KR) .................. 10-2015-0140526

(51) Int. Cl.
*G06K 9/00* (2006.01)
*G06T 3/00* (2006.01)
(Continued)

(52) U.S. Cl.
CPC ............ *G06T 3/0068* (2013.01); *A61B 6/469* (2013.01); *A61B 6/547* (2013.01); *A61B 8/4245* (2013.01);
(Continued)

(58) Field of Classification Search
CPC ... G06T 3/0068; G06T 7/0012; G06T 7/0014; G06T 7/30; G06T 3/0075; G06T 7/33;
(Continued)

(56) References Cited

U.S. PATENT DOCUMENTS 5,672,877 A * 9/1997 Liebig ................. A61B 6/5235
250/363.04
7,020,313 B2 * 3/2006 Declerck ............... G06T 7/0024
382/128
(Continued)

*Primary Examiner* — Eric Rush
(74) *Attorney, Agent, or Firm* — Sughrue Mion, PLLC

(57) ABSTRACT

There are provided an image processing apparatus for registering medical images having different modalities and a method for controlling the same. A reference location is designated in advance, a pre-designated cross-sectional image of an object is used, a corresponding location is extracted, and then image registration is performed. The image processing apparatus according to an exemplary embodiment includes a communication unit configured to receive a first medical image and a second medical image having a different modality from the first medical image of an object from a first medical apparatus and a second medical apparatus, respectively; and an image processing unit configured to extract a pre-designated cross-sectional image from the second medical image, extract a location corresponding to a reference location of the object from the extracted cross-sectional image, and perform registration of the second medical image and the first medical image corresponding to the extracted cross-sectional image.

17 Claims, 20 Drawing Sheets

(51) Int. Cl.
  *A61B 34/20* (2016.01)
  *A61B 90/00* (2016.01)
  *G06T 7/30* (2017.01)
  *A61B 8/00* (2006.01)
  *G06T 7/00* (2017.01)
  *G06T 7/33* (2017.01)
  *A61B 6/00* (2006.01)
  *A61B 8/08* (2006.01)

(52) U.S. Cl.
  CPC ........ *A61B 8/5238* (2013.01); *A61B 8/5261* (2013.01); *A61B 34/20* (2016.02); *A61B 90/36* (2016.02); *A61B 90/37* (2016.02); *G06T 7/0012* (2013.01); *G06T 7/30* (2017.01); *G06T 7/33* (2017.01); *G06T 7/337* (2017.01); *A61B 2034/2048* (2016.02); *A61B 2034/2055* (2016.02); *A61B 2090/364* (2016.02); *A61B 2090/378* (2016.02); *G06K 2209/05* (2013.01); *G06T 2207/10072* (2013.01); *G06T 2207/10116* (2013.01); *G06T 2207/10132* (2013.01); *G06T 2207/30004* (2013.01)

(58) Field of Classification Search
  CPC ........... G06T 7/337; G06T 2207/10072; G06T 2207/10116; G06T 2207/10132; G06T 2207/30004; G06K 2209/05; A61B 6/02; A61B 6/12; A61B 6/4417; A61B 6/46; A61B 6/461; A61B 6/463; A61B 6/464; A61B 6/469; A61B 6/5223; A61B 6/5229; A61B 6/5235; A61B 6/5247; A61B 6/547; A61B 8/0833; A61B 8/0841; A61B 8/085; A61B 8/4245; A61B 8/4254; A61B 8/4416; A61B 8/46; A61B 8/461; A61B 8/483; A61B 8/5238; A61B 8/5261; A61B 34/20; A61B 90/36; 90/37; A61B 2034/2048; A61B 2034/2055; A61B 2090/364; A61B 2090/378
  USPC ....... 382/128, 131, 132, 154, 282, 291, 294; 600/407, 425, 426
  See application file for complete search history.

(56) References Cited

U.S. PATENT DOCUMENTS

| Patent/Pub No. | Date | Inventor | Classification |
|---|---|---|---|
| 7,627,158 B2 * | 12/2009 | Hay | G06T 7/33 382/131 |
| 8,731,264 B2 * | 5/2014 | Kruecker | G06T 7/30 382/131 |
| 9,558,549 B2 * | 1/2017 | Ishikawa | G06T 7/12 |
| 10,026,191 B2 * | 7/2018 | Accomando | G06T 7/33 |
| 2006/0072808 A1 * | 4/2006 | Grimm | G06T 7/33 382/151 |
| 2007/0010743 A1 * | 1/2007 | Arai | G06T 7/33 600/443 |
| 2009/0054772 A1 * | 2/2009 | Lin | A61N 7/02 600/439 |
| 2009/0097778 A1 * | 4/2009 | Washburn | G06T 7/33 382/294 |
| 2009/0175518 A1 * | 7/2009 | Ikuma | A61B 8/4254 382/128 |
| 2009/0259230 A1 * | 10/2009 | Khadem | A61B 19/5244 606/130 |
| 2009/0303252 A1 * | 12/2009 | Hyun | G06T 7/33 382/131 |
| 2010/0036247 A1 * | 2/2010 | Yamamoto | A61B 8/4254 600/443 |
| 2010/0067768 A1 * | 3/2010 | Ionasec | G06T 7/35 382/131 |
| 2010/0174192 A1 * | 7/2010 | Azuma | A61B 6/5247 600/443 |
| 2010/0239150 A1 * | 9/2010 | Ishikawa | G06T 7/254 382/131 |
| 2011/0134113 A1 * | 6/2011 | Ma | G06T 7/13 345/419 |
| 2012/0035462 A1 * | 2/2012 | Maurer, Jr. | A61B 6/5247 600/411 |
| 2012/0099770 A1 * | 4/2012 | Cagnan | A61B 19/50 382/128 |
| 2012/0262453 A1 * | 10/2012 | Endo | A61B 8/5246 345/419 |
| 2012/0310092 A1 * | 12/2012 | Yawata | A61B 8/00 600/443 |
| 2013/0034203 A1 * | 2/2013 | Wang | G06T 7/0032 382/132 |
| 2014/0193053 A1 * | 7/2014 | Kadoury | G06T 11/008 382/131 |
| 2015/0051489 A1 * | 2/2015 | Caluser | A61B 8/0825 600/440 |
| 2015/0070469 A1 * | 3/2015 | Yoshibayashi | G06T 7/0012 348/46 |
| 2015/0182191 A1 * | 7/2015 | Caluser | A61B 8/5238 600/440 |
| 2015/0223777 A1 * | 8/2015 | Rasoulian | G06T 7/33 345/424 |
| 2016/0100773 A1 * | 4/2016 | Ching | A61B 34/20 600/424 |

* cited by examiner (a)

(b)

(a) (b)

(a)

(b)

METHOD AND APPARATUS FOR REGISTRATION OF MEDICAL IMAGES

CROSS-REFERENCE TO RELATED APPLICATION(S)

This application claims priority from Korean Patent Application No. 10-2014-0136091, filed on Oct. 8, 2014 in the Korean Intellectual Property Office, and from Korean Patent Application No. 10-2015-0140526, filed on Oct. 6, 2015 in the Korean Intellectual Property Office, the disclosures of which are incorporated herein by reference in their respective entireties.

BACKGROUND

1. Field

Exemplary embodiments relate to an image processing apparatus, a method for controlling an image processing apparatus, and a medical imaging apparatus, and to an apparatus and method for registering medical images having different modalities.

2. Description of the Related Art

According to the recent development of medical technology, it is possible to obtain a medical image of a high resolution. As fine manipulation of medical apparatuses is possible, a method in which a small hole is formed in a skin without incision for exposing an area to be tested, a catheter or a medical needle is directly inserted into a blood vessel or a desired body area, and treatment is performed while an inside of the body is observed using a medical imaging device has been developed. This method is referred to as "a procedure method using an image" or "an interventional image procedure method."

A practitioner identifies a location of an organ or a lesion from an image. In addition, a patient may breathe or move while a procedure is performed, and a change resulting therefrom should be identified. Therefore, the practitioner needs to perform a procedure by identifying breathing or movement accurately and rapidly, based on a real time image. In this case, it is difficult to identify shapes of organs and lesions in an ultrasound real time image with the naked eye.

SUMMARY

An apparatus and method for registering a plurality of medical images having different modalities are provided to perform automatic registration rapidly and conveniently by using a cross section in a three-dimensional (3D) volume image.

According to an aspect of one or more exemplary embodiments, there is provided an image processing apparatus, including a communicator configured to receive a first medical image of an object from a first medical apparatus and to receive a second medical image of the object from a second medical apparatus; and an image processor configured to extract a pre-designated cross-sectional image from the second medical image, to extract a location that corresponds to a reference location of the object from the extracted cross-sectional image, and to perform a registration of the second medical image with respect to the first medical image based on the extracted cross-sectional image or the extracted corresponding location.

The first medical image may include at least one from among an ultrasound image, an optical coherence tomography (OCT) image, a computed tomography (CT) image, a magnetic resonance (MR) image, an X-ray image, a single photon emission computed tomography (SPECT) image, a positron emission tomography (PET) image, a PET-CT image, fluoroscopy image, and a C-arm image, and the second medical image may include at least one from among an ultrasound image, an OCT image, a CT image, an MR image, an SPECT image, a PET image, PET-CT image, fluoroscopy image, X-ray image and a C-arm image.

The reference location may refer to a location of a navigator placed on the object.

The navigator may include at least one from among an ultrasound probe, an optical tracker and a procedure tool in which a sensor configured for setting a location is mounted.

The image processor may be further configured to perform image processing which relates to at least one anatomical object shown in the extracted cross-sectional image and to extract a location that corresponds to the reference location.

The image processor may be further configured to use the corresponding location to extract an intersecting location that intersects at a skin line.

The intersecting location may be an intersecting point in an axial direction in which the navigator is located with respect to the corresponding location.

The image processor may be further configured to provide location data that corresponds to the reference location of the navigator in the extracted cross-sectional image.

The image processor may be further configured to extract an anatomically corresponding location in each of the first medical image and the second medical image.

The anatomically corresponding location in each of the first medical image and the second medical image may correspond to a location included in the cross-sectional image extracted from the second medical image.

The image processor may be further configured to provide anatomically corresponding location data in each of the first medical image and the second medical image when the anatomically corresponding location is not extracted.

The image processing apparatus may further include a display configured to display a registered image by using the reference location of the object or an intersecting location that intersects at a skin line.

According to another aspect of one or more exemplary embodiments, there is provided a method for controlling an image processing apparatus, including: receiving, from a first medical apparatus, a first medical image of an object, and receiving, from a second medical apparatus, a second medical image of the object; extracting a pre-designated cross-sectional image from the second medical image and extracting a location that corresponds to a reference location of the object from the extracted cross-sectional image; and performing a registration of the second medical image with respect to the first medical image based on the extracted cross-sectional image or the extracted corresponding location.

The reference location may refer to a location of a navigator placed on the object.

In the extracting of the corresponding location, image processing that relates to at least one anatomical object shown in the extracted cross-sectional image may be performed to extract a location that corresponds to a reference location of a navigator.

The method may further include extracting an intersecting location that intersects at a skin line by using the corresponding location.

The intersecting location may be an intersecting point in an axial direction in which the navigator is located with respect to the corresponding location.

The method may further include providing location data that corresponds to a reference location of a navigator in the extracted cross-sectional image.

The method may further include extracting an anatomically corresponding location in each of the first medical image and the second medical image based on a location included in the cross-sectional image extracted from the second medical image.

The method may further include extracting anatomically corresponding location data when the anatomically corresponding location is not extracted.

According to still another aspect of one or more exemplary embodiments, there is provided a medical imaging apparatus, including a probe configured to obtain a first medical image of an object; a sensor configured to detect a reference location of a probe placed on the object; and an image processor configured to extract a pre-designated cross-sectional image from a second medical image that has a different modality from the first medical image, to extract a location that corresponds to a reference location of the object from the extracted cross-sectional image, and to perform a registration of the second medical image with respect to the first medical image based on the extracted cross-sectional image or the extracted corresponding location.

The sensor may be further configured to detect coordinate information that relates to a location and a direction of the probe with respect to the object.

The specific location and direction may be a location and direction of the probe when an axis of the probe is parallel with an axis of the object and the probe is located on a reference point of the object.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
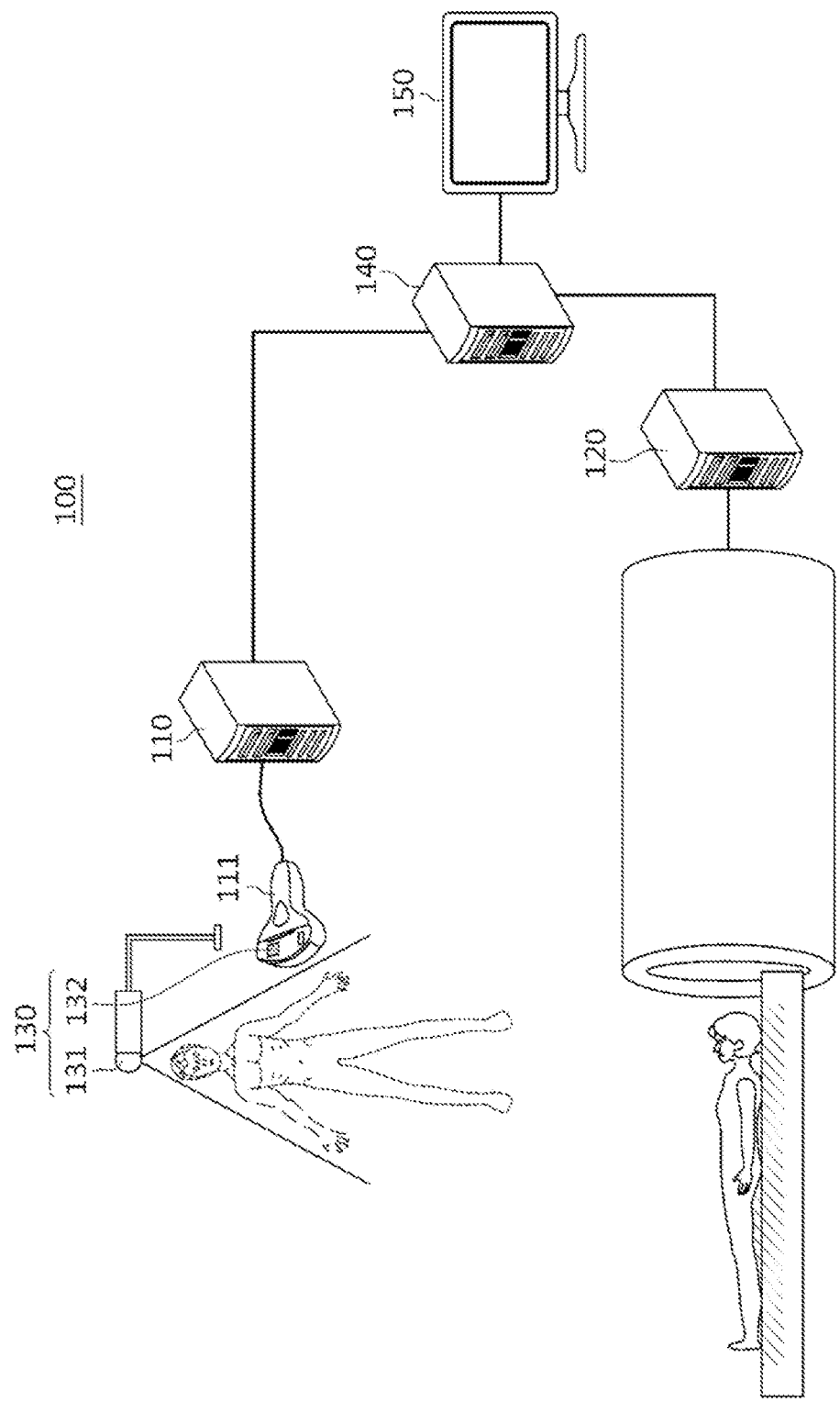
FIG. 1 is a diagram illustrating a medical image processing system, according to an exemplary embodiment.

Advantages and features of the present inventive concept, and methods of achieving the same will be clearly understood with reference to the accompanying drawings and the following detailed exemplary embodiments.

Embodiments described in this specification and configurations illustrated in drawings are only exemplary examples. It is understood that the present inventive concept covers various modifications that can substitute for the exemplary embodiments presented herein and drawings at the time of filing of this application.

Hereinafter, an ultrasound imaging apparatus and a method of controlling the same according to exemplary embodiments to be described will be described with reference to the accompanying drawings. The same reference number refers to the same component in the drawings. Redundant description thereof will be omitted.

In this specification, the term "object" may include a human, an animal, or a part thereof. The object may include, for example, an organ such as a liver, a heart, a uterus, a brain, a breast or an abdomen or a blood vessel. In addition, in this specification, the term "user" may be a doctor, a nurse, a clinical pathologist, a medical image professional, or a technician who repairs a medical apparatus, but the exemplary embodiments are not limited thereto.

In addition, a reference location described hereinafter may include a reference point, a corresponding location may include a corresponding point, and an intersecting location may include an intersecting point.

Necessity of registration of different images having different modalities will be exemplified. An ultrasound image has a real-time property, but it is difficult to clearly identify an organ and a lesion. Conversely, in a magnetic resonance (MR) image or a computerized tomography (CT) image, it is possible to clearly identify an organ and a lesion. However, since it is difficult obtain an image in real time during a medical procedure, there is a problem in that a patient's respiration and movement occurring during a medical procedure are not reflected. In addition, in the ultrasound image, a recognition rate of soft tissues, such as a liver or a lung, is higher than a corresponding recognition rate of hard tissues, such as bones. However, in the CT image, a recognition rate of hard tissues is higher than that of soft tissues.

Therefore, there is a need to register images having different modalities while maintaining the advantages of each of the images. When a plurality of images having different modalities are registered, it is sometimes difficult to register the images according to an image quality thereof. A registration method was discussed to address such problems.

FIG. 1 is a diagram illustrating a medical image processing system, according to an exemplary embodiment.

As illustrated in FIG. 1, an image processing system 100 includes a first medical apparatus 110, a second medical apparatus 120, a detecting device 130, an image processing apparatus (also referred to herein as an "image processor") 140 and a display unit (also referred to herein as a "display device" and/or as a "display") 150.

According to the exemplary embodiment, the first medical apparatus 110 may be an apparatus that is configured for generating an image in a process of interventional medical procedures on a patient. The first medical apparatus 110 may include a medical apparatus such as an ultrasound imaging apparatus or an optical coherence tomography (OCT) imaging apparatus, and also include any of a computed tomography (CT) imaging apparatus, a magnetic resonance (MR) imaging apparatus, an X-ray imaging apparatus, a single photon emission computed tomography (SPECT) imaging apparatus, a positron emission tomography (PET) imaging apparatus and a C-arm imaging apparatus. However, the exemplary embodiment of the first medical apparatus is not limited to any of the exemplified medical apparatuses. The second medical apparatus 120 may include any of the OCT imaging apparatus, the CT imaging apparatus, the MR imaging apparatus, the SPECT imaging apparatus, the PET imaging apparatus and the C-arm imaging apparatus.

The first medical apparatus 110 and the second medical apparatus 120 generate a first medical image and a second medical image, respectively, and provide the image to the image processing apparatus 140. The first medical image and the second medical image have different modalities. The different modality denotes that the first medical image and the second medical image are different types. In this aspect, the first medical image and the second medical image may have different generation methods and principles. The image processing apparatus 140 obtains the first medical image and the second medical image and performs registration of the first medical image with respect to the second medical image, wherein the two medical images have different modalities. The image registered by the image processing apparatus 140 may be displayed via the display unit 150.

Hereinafter, while a case in which the first medical apparatus 110 is an ultrasound imaging apparatus will be exemplified, the first medical apparatus 110 is not limited to the ultrasound imaging apparatus. When the first medical apparatus 110 is an apparatus such as the MR imaging apparatus or the CT imaging apparatus rather than the ultrasound imaging apparatus, a procedure tool having a sensor that is capable of navigating a location, such as an optical tracker, may be used instead of an ultrasound probe in order to set a reference location of the object and calculate location information.

When the first medical apparatus 110 is the ultrasound imaging apparatus, the first medical image of a volume of interest of the object may be provided in real time. For example, when deformation and displacement of the organ resulting from a body activity of the object occur, a change in the first medical image occurs in real time. However, in the first medical image, it is sometimes difficult to clearly observe all organs and lesions, and it is difficult to identify deformation and displacement of the organ by using only the first medical image. Therefore, by performing a registration of the first medical image with respect to the second medical image that has a different modality, such as the CT image or the MR image, a location of the organ or a location of the lesion may be clearly distinguished.

The first medical apparatus 110 generates an ultrasound image by radiating ultrasound energy onto the object and detecting a reflected ultrasound signal by using an ultrasound probe 111. In general, the probe 111 may include a piezoelectric transducer, but the exemplary embodiments are not limited thereto. The probe 111 may include a capacitive micromachined ultrasonic transducer (cMUT) that converts between ultrasound and an electrical signal via a change in capacitance, a magnetic micromachined ultrasonic transducer (mMUT) that converts between ultrasound and an electrical signal via a change in a magnetic field, an optical ultrasound detector that converts between ultrasound and an electrical signal via a change in an optical property, and the like.

When ultrasound energy in the range of several to several hundreds of MHz is delivered to a specific area inside the patient's body from the probe 111, this ultrasound energy is partially reflected from layers between several different tissues. The ultrasound energy is reflected from subjects that have a density change inside the body, for example, blood cells in blood plasma and small tissues (structures) inside organs.

The ultrasound energy reflected in this manner causes vibrations in a converter of the probe 111, and the converter outputs electrical pulses according to such vibrations. Such electrical pulses are converted into an image. When subjects have different ultrasound reflection properties, each of the subjects may be represented at different brightness values in an ultrasound image of a B mode. The second medical apparatus 120 may generate the second medical image of a volume of interest (VOI) of the object, and the second medical image may be imaged in advance before the medical procedure is performed.

As described above, the second medical apparatus 120 may include any of the OCT imaging apparatus, the CT imaging apparatus, the MR imaging apparatus, the SPECT imaging apparatus, the PET imaging apparatus and the C-arm imaging apparatus. For convenience of description, while it is assumed in the following exemplary embodiment that the second medical image is the MR image or the CT image, the exemplary embodiments are not limited thereto.

The CT image or the MR image generated in the second medical apparatus 120 has an advantage in that a location of the organ or a location of the lesion is clearly distinguished. However, in the CT image or the MR image, the organ may be deformed or dislocated when the patient breathes or turns during the procedure, but such deformation and displacement of the organ according to movement of the patient may not be reflected to the image in real time.

Medical images imaged by the first medical apparatus 110 or the second medical apparatus 120 may include 2D cross sections or 3D images generated by accumulating 2D cross sections. For example, the first medical apparatus 110 may generate the 2D cross section, or may generate the 3D image by hand sweeping or wobbling the probe 111 or through the probe 111 of a 2D array method. Also, the second medical apparatus 120 images a plurality of cross sections while changing a location or an orientation of the cross section. When such cross sections are accumulated, image data of a 3D volume that represents a specific area of the patient's body three-dimensionally may be generated. A method in which cross sections are accumulated and image data of a 3D volume is generated in this manner is referred to as a multiplanar reconstruction (MPR) method. The second medical image may include a contrast-enhanced image in which the contrast is enhanced in order to increase brightness of an organ of interest of the patient. Hereinafter, for convenience of description, it is assumed that the first medical image is the 2D image and the second medical image is the 3D image.

The detecting device 130 may detect the reference location of the object that may be represented as the first medical image. For example, the detecting device 130 may detect at least one of a location and a direction of the probe 111, and may also detect movement of the probe 111. The reference location is a set location of the object. For example, in order to scan a solar plexus area of the object, a location at which the solar plexus may be scanned may be set as the reference location of the object. The detecting device 130 may include a magnetic field generator 131 and a sensor 132 configured to detect a change in the magnetic field. The magnetic field generator 131 may be fixed to a specific location of the first medical apparatus 110, and the sensor 132 may be disposed on the probe 111. Therefore, the detecting device 130 may detect at least one of the location and the direction of the probe 111 from a relative location relation between the sensor 132 and the magnetic field generator 131. In addition, the detecting device 130 may include any of an optical sensor, an accelerometer sensor, a tilt sensor, or the like which is configured to detect at least one of the location and the direction of the probe 111. The detecting device 130 may calculate at least one of the location and the direction of the probe 111 as coordinate information in a coordinate system of the detecting device 130.

The image processing apparatus 140 registers cross-sectional images extracted from the first medical image obtained from the first medical apparatus 110 with respect to the second medical image obtained from the second medical apparatus 120. Registration of medical images may include an operation in which a coordinate system of the detecting device 130 and a coordinate system of the second medical image are mapped to each other. Movement of the probe 111 has a one-to-one correspondence with a view of the first medical image. Also, the user more easily performs control of movement of the probe 111 than control of the first medical image. Therefore, the system according to the exemplary embodiment may detect a reference location of the probe 111 placed on the object and extract a corresponding location of the second medical image that corresponds to the reference location of the probe 111. In addition, when an intersecting point that is a location that intersects at a skin line 500 is extracted from the extracted corresponding location of the second medical image, it is possible to register medical images of different types. The corresponding location is a location in the second medical image corresponding to the reference location of the object that may be displayed in the first medical image. Since image registration is performed by detecting the reference location of the probe 111, it is possible to register images, regardless of resolutions of medical images.

In the exemplary embodiment, the registered image may be a fusion image in which the first medical image and the second medical image are fused. In another exemplary embodiment, the registered image may be an image in which the first medical image and the second medical image at the same observation viewpoint are disposed in parallel. The registered image may be displayed on the display unit 150.

In the exemplary embodiment illustrated in FIG. 1, each of the first medical apparatus 110, the detecting device 130, the image processing apparatus 140 and the display unit 150 is configured as an independent apparatus, but this is only for convenience of description. The first medical apparatus 110, the detecting device 130 and the display unit 150 may also be implemented as a single apparatus.

Meanwhile, in order to extract a cross section of the second medical image corresponding to the reference location of the probe 111 and extract a location intersecting at the skin line 500 corresponding to the reference location, an axis of the probe 111 may be disposed in parallel with an axis of the object. Here, the axis of the probe 111 may be divided into at least two axes that are perpendicular to each other around the probe 111, and may be the same as a coordinate axis of a cross section of the first medical image obtained via the probe 111. For example, two axes of the probe 111 may include a first axis that is a forward direction of the ultrasound and a second axis orthogonal to the first axis. In addition, the axis of the object may be divided into at least two axes that are perpendicular to each other around the object, and may be the same as a coordinate axis of the second medical image. A plane including the two axes of the object may be divided into a sagittal plane including a middle sagittal plane, a coronal plane and a transverse plane. The above three planes may be reference planes of the object.

Also, a center of the probe 111 may be located above the reference location of the object. Here, the center of the probe 111 may refer to a center of a plane from which ultrasound energy is transmitted among planes of the probe 111. Here, the reference location may be at least one of subjects of the object. The reference location may be a subject that is easily identified in the first and second medical images and may not be deformed over time. For example, the reference location may be a bone, among subjects of the object.

Figure 2:
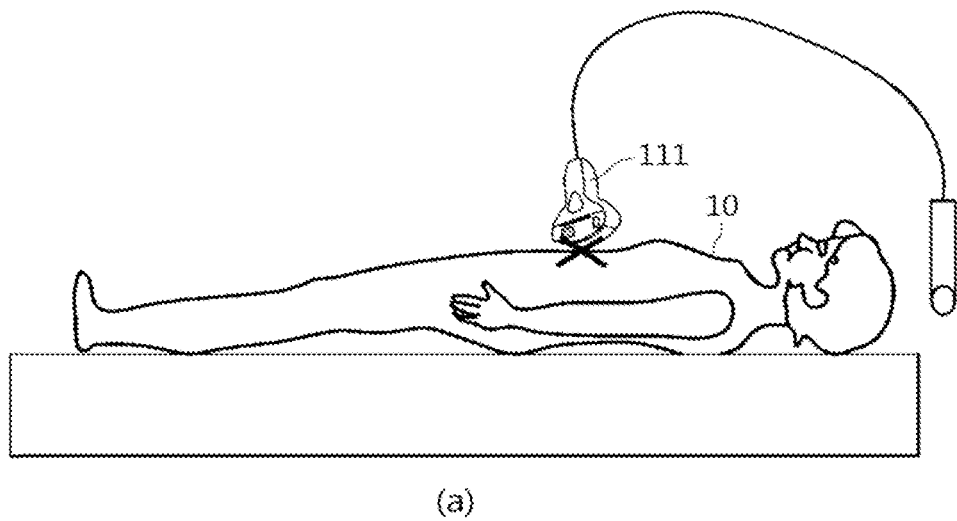
FIG. 2 is a diagram illustrating a case in which an ultrasound probe is placed on an object and a reference location of a first medical image is detected, according to an exemplary embodiment.
Figure 2:
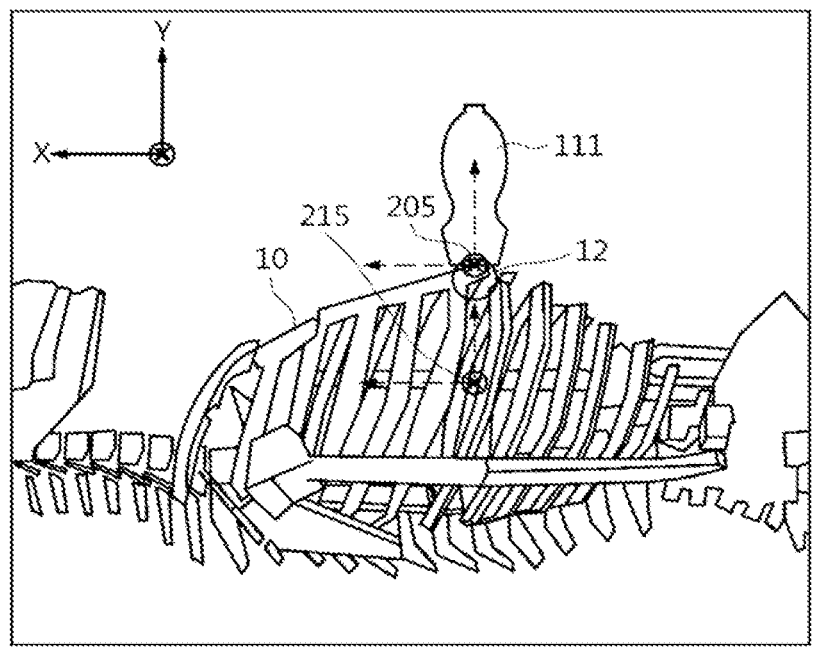

FIG. 2 is a diagram illustrating a case in which an ultrasound probe is placed on an object and a reference location of a first medical image is detected, according to an exemplary embodiment.

As illustrated in drawing (a) of FIG. 2, the user may place the probe 111 on an object 10, and specifically, as illustrated in drawing (b) of FIG. 2, may place the probe 111 on a solar plexus 12 among subjects of the object 10. In this case, a point at which the probe 111 is placed on the object may serve as the reference location of the object. In addition, the user may set an axis 205 of the probe 111 to be parallel with an axis 215 of the object.

When the probe 111 is placed on the reference location of the object and the axis of the probe 111 is parallel with the axis of the object, the detecting device 130 may calculate coordinate information relating to the probe 111. The coordinate information relating to the probe 111 includes coordinate information in the coordinate system of the detecting device 130, and may include at least one of location information and direction information relating to the probe 111. For convenience of description, the coordinate information relating to the probe 111 will be described.

The image processing apparatus 140 may calculate coordinate information relating to an intersecting location and a corresponding location of the second medical image in the coordinate system of the second medical image. An axis of the second medical image may be the same as an axis of the object. Therefore, when a relation between coordinate information relating to the probe 111 placed at the reference location and coordinate information relating to the corresponding location and the intersecting location in the second medical image is calculated, a relation between the coordinate system of the detecting device 130 and the coordinate system of the second medical image may be obtained.

Figure 3:
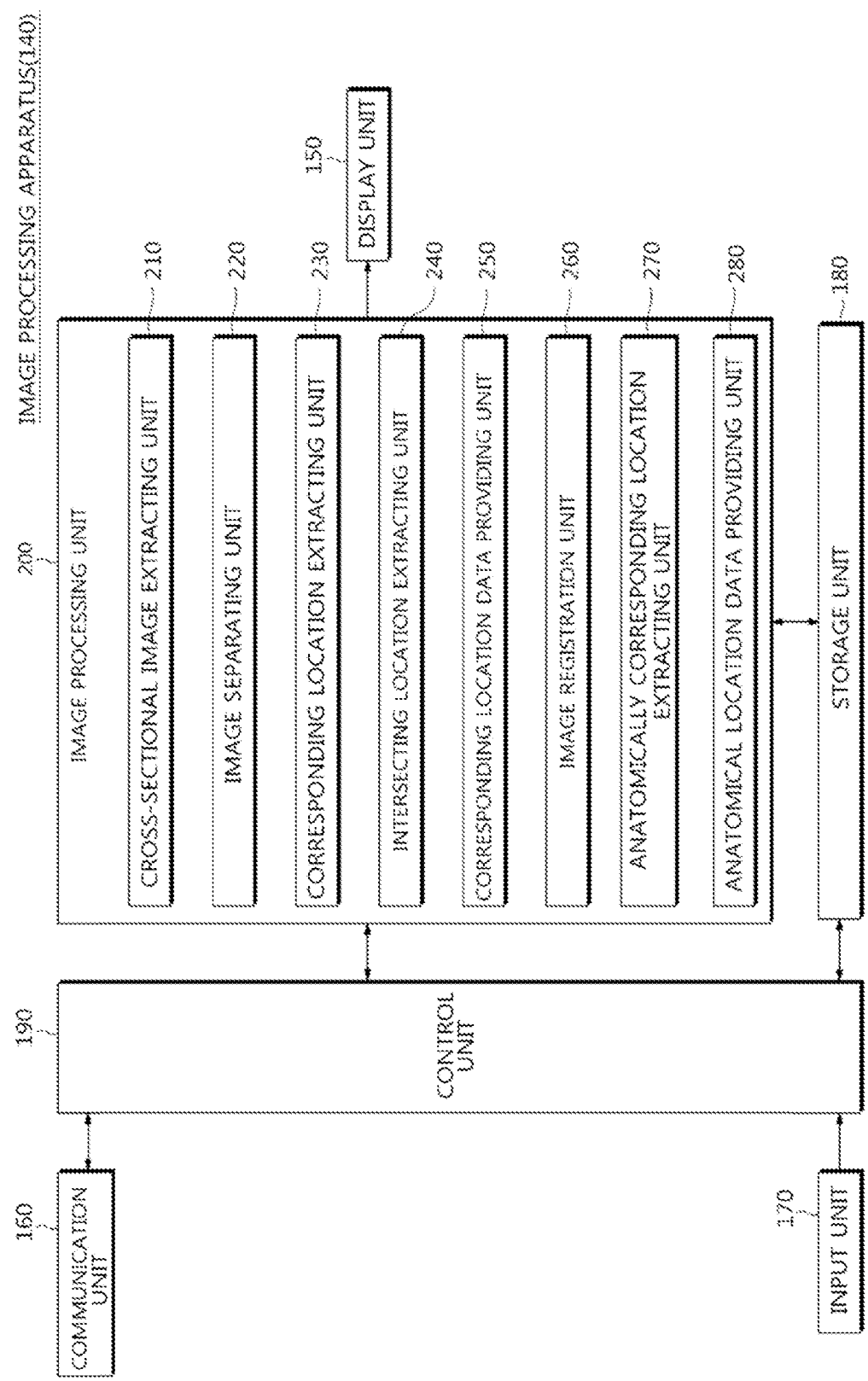
FIG. 3 is a control block diagram illustrating a configuration of an image processing apparatus.

FIG. 3 is a control block diagram illustrating a configuration of an image processing apparatus.

As illustrated in FIG. 3, the image processing apparatus 140 may include a communication unit (also referred to herein as a "communicator" and/or as a "transceiver") 160, an input unit (also referred to herein as an "input device") 170, a storage unit (also referred to herein as a "storage device" and/or as a "storage") 180, a control unit (also referred to herein as a "controller") 190 and an image processing unit (also referred to herein as an "image processor") 200. However, all illustrated components are not essential components, and other general-purpose components may be further included in addition to the illustrated components.

The communication unit 160 may receive the first medical image and the second medical image from the first medical apparatus 110 and the second medical apparatus 120, respectively, and receive at least one of location information and direction information relating to the probe 111 from the detecting device 130. The communication unit 160 may include an interface configured to obtain the first medical image and the second medical image from the first medical apparatus 110 and the second medical apparatus 120, respectively. The interface refers to an interface (not illustrated) that is configured for providing a direct or indirect connection with the first medical apparatus 110 and the second medical apparatus 120.

The interface may obtain the first medical image imaged by the first medical apparatus 110 in real time, and may be directly connected to the second medical apparatus 120 in order to obtain the second medical image that is imaged by the second medical apparatus 120 in advance before the medical procedure. In addition, the interface may obtain the second medical image via other external storage media (such as a USB, a CD or a DVD) or via a network. The communication unit 160 may store the obtained second medical image in the storage unit 180.

In addition, the interface may receive coordinate information relating to the probe 111 from the detecting device 130.

The communication unit 160 may perform data communication with other apparatus according to any of various wired and/or wireless communication protocols, and preferably, perform data communication according to a digital imaging and communications in medicine (DICOM) standard.

The input unit 170 may receive an input for manipulating the image processing apparatus 140 from the user, and may include any of a button, a keypad, a switch, a dial, and/or a touch interface in order to enable the user to directly manipulate the image processing apparatus 140. The input unit 170 may include a display panel for displaying an image and may be implemented as a touch screen.

The control unit 190 controls overall operations of the image processing apparatus 140. For example, the control unit 190 may perform control such that the image processing unit 200 generates and registers images by using a user command input via the input unit 170, data received via the communication unit 160, and/or a program stored in the storage unit 180. In addition, the control unit 190 may perform control such that the image processed by the image processing unit 200 is displayed on the display unit 150.

The image processing unit 200 may include a cross-sectional image extracting unit (also referred to herein as a "cross-section image extractor") 210, an image separating unit (also referred to herein as an "image separator") 220, a corresponding location extracting unit (also referred to herein as a "corresponding location extractor") 230, an intersecting location extracting unit (also referred to herein as an "intersecting location extractor") 240, a corresponding location data providing unit (also referred to herein as a "corresponding location data provider") 250, an image registration unit (also referred to herein as an "image registerer") 260, an anatomically corresponding location extracting unit (also referred to herein as an "anatomically corresponding location extractor") 270 and an anatomical location data providing unit (also referred to herein as an "anatomical location data provider") 280.

The cross-sectional image extracting unit 210 extracts a pre-designated cross-sectional image from the second medical image. The cross-sectional image includes a 2D MR or CT image in the second medical apparatus 120. As described above, medical images imaged by the second medical apparatus may be 2D cross sections or 3D images generated by accumulating 2D cross sections. Therefore, a cross-sectional image may be extracted from pre-imaged medical images of 2D cross sections, or a cross-sectional image may be extracted from the 3D image. In the following exemplary embodiment, a case in which the cross-sectional image is extracted from the 3D image will be exemplified.

The image separating unit 220 segments anatomical objects shown in the cross-sectional image that are extracted from the second medical image. Segmentation is a type of image processing and refers to separation of each of the anatomical objects from a background image. By performing segmentation, information that may be used to extract a corresponding location may be obtained.

The corresponding location extracting unit 230 uses information relating to the segmentation performed by the image separating unit 220 and extracts a location corresponding to the reference location of probe placed on the object from the second medical image.

The intersecting location extracting unit 240 extracts the corresponding location extracted by the corresponding location extracting unit 230 and a location intersecting at the skin line 500 of the object. Since the corresponding location extracted via segmentation may be a point inside the body, a corresponding point at the skin line 500 may be extracted to be registered to the reference location of the probe 111 in the first medical image.

When a location corresponding to the reference location of the probe 111 is not extracted from the cross-sectional image extracted from the second medical image, the corresponding location data providing unit 250 may provide data relating to the location corresponding to the reference location of the probe 111.

The image registration unit 260 may generate a registration image by registering the reference location in which the probe 111 is located in the first medical image with respect to the corresponding location of the cross-sectional image extracted from the second medical image or the intersecting location extracted from provided location data.

The anatomically corresponding location extracting unit 270 may additionally automatically extract an anatomically corresponding location in each of the first medical image and the second medical image from the first medical image and the second medical image.

The anatomical location data providing unit 280 may provide anatomical location data when the anatomically corresponding location is not automatically or manually extracted from the first medical image and the second medical image.

The storage unit 180 may store pre-input data and data calculated when image processing is performed according to the exemplary embodiment. The storage unit 180 may store the first medical image and the second medical image received by the communication unit 160, and may store the 2D cross-sectional image and the 3D image of the object generated by the second medical apparatus 120. In addition, the storage unit 180 may store information relating to the reference location of the probe 111 placed on the object as a coordinate value, and store anatomical information, location information, brightness information and the like of anatomical objects to be segmented. Also, the storage unit 180 may store data relating to a location corresponding to the reference location of the probe placed on the object.

The storage unit 180 may be implemented as any of a non-volatile memory device such as a read only memory (ROM), a programmable read only memory (PROM), an erasable programmable read only memory (EPROM), and/ or as a flash memory, a volatile memory device such as a random access memory (RAM), and/or as a storage device such as a hard disk or an optical disc, but the storage unit 180 is not limited thereto and may be implemented as any form known in the art.

Figure 4:
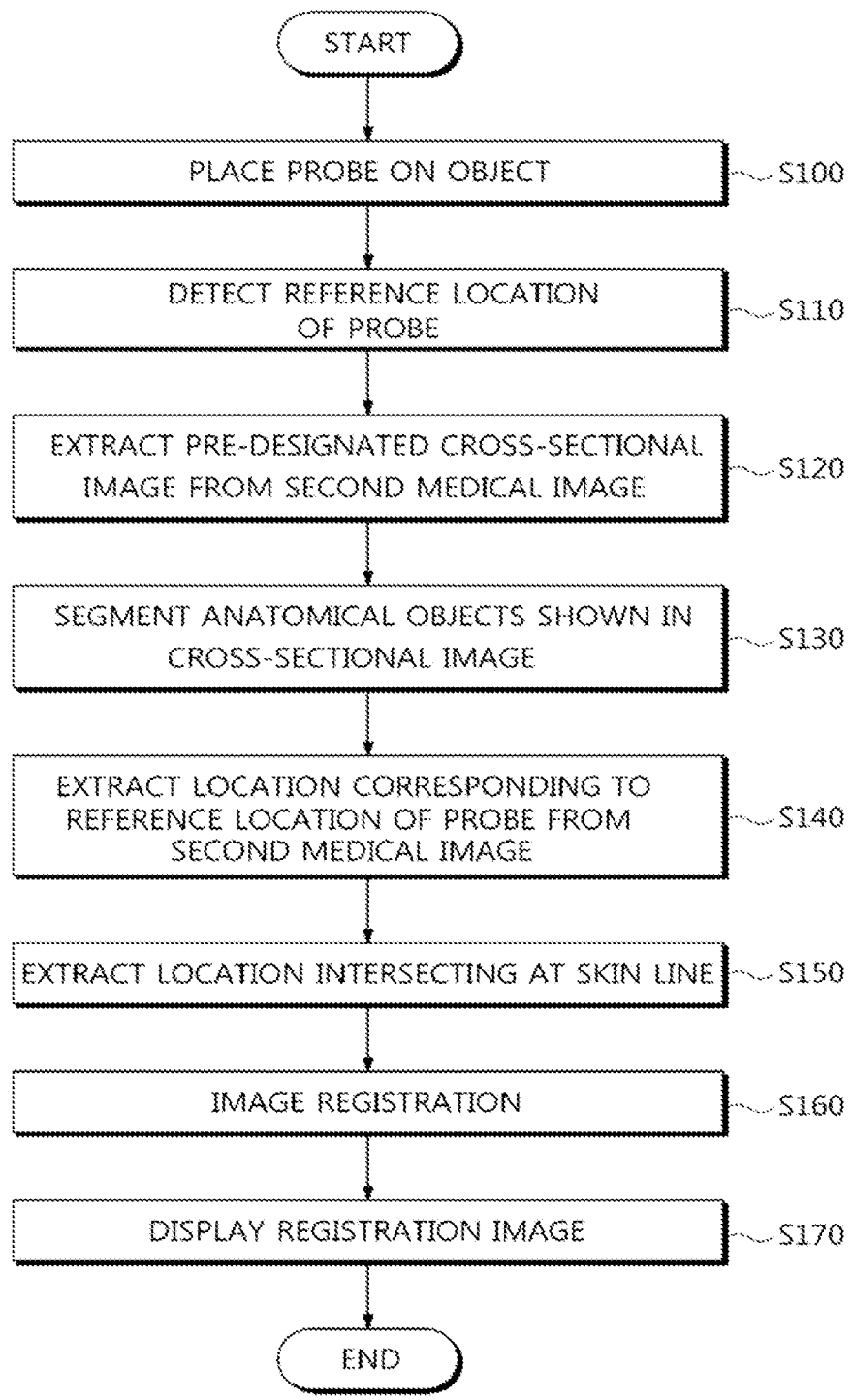
FIG. 4 is a flowchart illustrating an image processing method, according to an exemplary embodiment.

FIG. 4 is a flowchart illustrating an image processing method, according to an exemplary embodiment.

The image processing method disclosed in FIG. 4 will be described in detail with reference to FIGS. 5, 6, 7, 8, 9, and 10.

The probe 111 may be placed on the object according to an exemplary embodiment. Subjects of the object may include any of various subjects. However, hereinafter, for convenience of description, a case in which the subject is the solar plexus 12 will be exemplified, but the exemplary embodiments are not limited thereto.

First, as illustrated in FIG. 4, in operation S100, the probe 111 may be placed on an area of the solar plexus 12 of the object. As described above in FIG. 2, the user may place the probe 111 on the solar plexus 12. In this case, the solar plexus 12 may be the reference location of the probe 111 on the object in the first medical image, and the axis 205 of the probe 111 may be set to be parallel with the axis 215 of the object.

In operation S110, the detecting device 130 may detect the reference location of the probe 111 in the object by detecting at least one of the location and the direction of the probe 111. As described above in FIG. 1, the detecting device 130 may include the magnetic field generator 131 and the sensor 132 configured to detect a change in the magnetic field. The detecting device 130 may detect the reference location of the probe 111 by detecting any of the location and the direction of the probe 111 from a relative location relation between the sensor 132 and the magnetic field generator 131, and may calculate the result as coordinate information in the coordinate system. Coordinate information of the reference location of the probe 111 detected in this manner is transmitted to the image processing apparatus 140 and used for image registration in operation S160, or, in operation S150, may be used to extract a location intersecting at the skin line 500 from a location corresponding to the reference location of the probe in the second medical image.

In operation S120, the cross-sectional image extracting unit 210 extracts a pre-designated cross-sectional image from the second medical image. As described above, medical images imaged by the second medical apparatus 120 may include 2D cross sections or 3D images generated by accumulating 2D cross sections. The cross-sectional image extracting unit 210 may use coordinate information of the reference location of the probe 111 detected by the detecting device 130 in order to extract the pre-designated cross-sectional image. In this case, the designated cross-sectional image may be extracted from statistical location information of the object. The statistical location information of the object will be exemplified with the area of the solar plexus 12. When a human's body is viewed from the outside, the solar plexus 12 is located at the center of the body. Based on information on the location of the solar plexus 12, a cross section including the corresponding location may be designated. In addition, from data of 2D cross-sectional images imaged by the second medical apparatus 120, a cross section including coordinate information of the reference location of the probe may be extracted.

Figure 5:
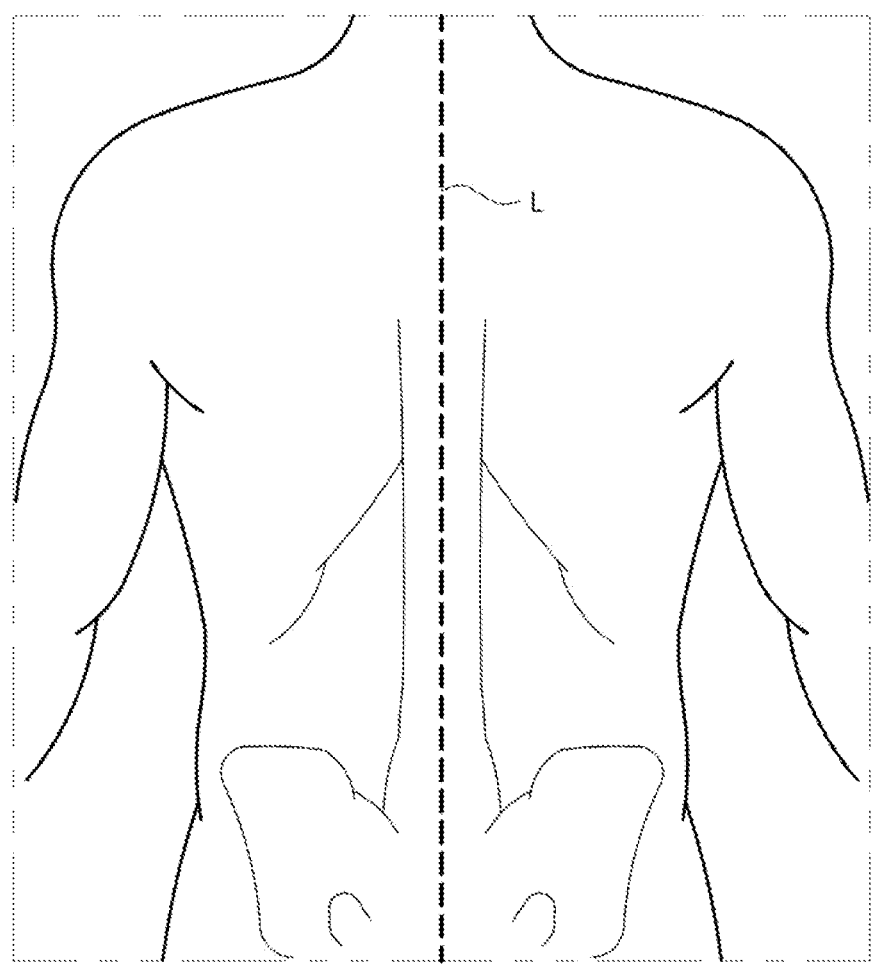
FIG. 5 is a diagram illustrating a case in which a cross-sectional image extracting unit sets a middle sagittal plane of a body as a reference plane in order to extract a cross section including a solar plexus area.

FIG. 5 is a diagram illustrating a case in which a cross-sectional image extracting unit sets a middle sagittal plane of a body as a reference plane in order to extract a cross section including a solar plexus area.

As illustrated in FIG. 5, an area (L) indicated by a dotted line represents a middle sagittal plane in which the solar plexus 12 is located. When the body is broadly divided into anatomical reference planes, the body is represented as a transverse plane, a coronal plane, and the like in addition to a plane including the middle sagittal plane. In the exemplary embodiment, a case in which a location including an area of the solar plexus 12 will be exemplified. Hereinafter, description will be made based on a plane including the middle sagittal plane, but the exemplary embodiments are not limited thereto, and a cross section to be extracted may be a cross section other than the middle sagittal plane. As the cross section, a cross section other than the middle sagittal plane may be extracted according to the reference location in which the probe 111 is located.

The cross-sectional image extracting unit 210 may extract a designated cross section from among 2D cross sections that are imaged by the second medical apparatus 120 in advance, and may extract a designated cross-sectional image from the 3D second medical image. As a method of extracting the cross-sectional image, a general image extracting method may be applied, but detailed description thereof will be omitted.

Figure 6:
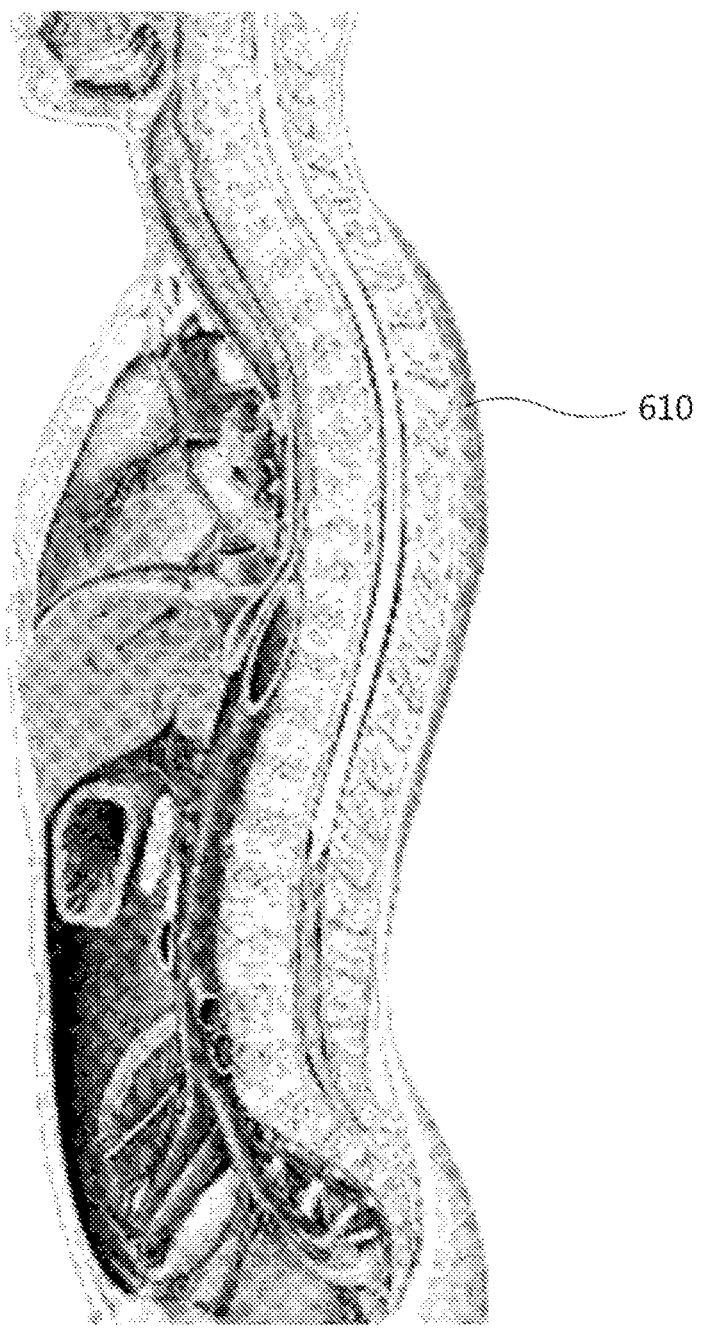
FIG. 6 is a diagram illustrating a case in which a cross-sectional image extracting unit extracts a pre-designated cross-sectional image from a second medical image.

FIG. 6 is a diagram illustrating a case in which a cross-sectional image extracting unit extracts a pre-designated cross-sectional image from a second medical image.

As illustrated in FIG. 6, an aspect 610 of a cross section extracted based on the middle sagittal plane may be identified.

Referring also to FIG. 4, in operation S130, the image separating unit 220 segments anatomical objects shown in the cross-sectional image from the cross-sectional image extracted by the cross-sectional image extracting unit 210. Segmentation is performed so that separate images of anatomical objects inside the body are obtained, and a location corresponding to the reference location of the probe is extracted from the second medical image. The anatomical objects refer to the body's components that can be identified in the medical image, such as any of an organ, a blood vessel, a lesion, a bone, a boundary surface between an organ and an organ, and the like. Segmentation is a type of image processing, and refers to separation of each of the anatomical objects from a background image. Information on an anatomical object to be segmented may be input in advance in the storage unit 180.

The image separating unit 220 may perform segmentation by using a graph cut technique or a Gaussian mixture model (GMM) technique. In the graph cut technique, a seed value of the background and a seed value of the anatomical object are used to gradually extend areas of a seed point of the background and a seed point of the anatomical object. During the extension, an area in which the area of the background and the area of the anatomical object meet is cut, and therefore the anatomical object is segmented. In the GMM technique, a color histogram of the medical image is represented as a plurality of Gaussian distribution models. Subsequently, a Gaussian distribution model of a specific area is selected in the histogram, and therefore anatomical objects are segmented. In addition to the above techniques, any of various segmentation techniques may be applied.

Figure 7:
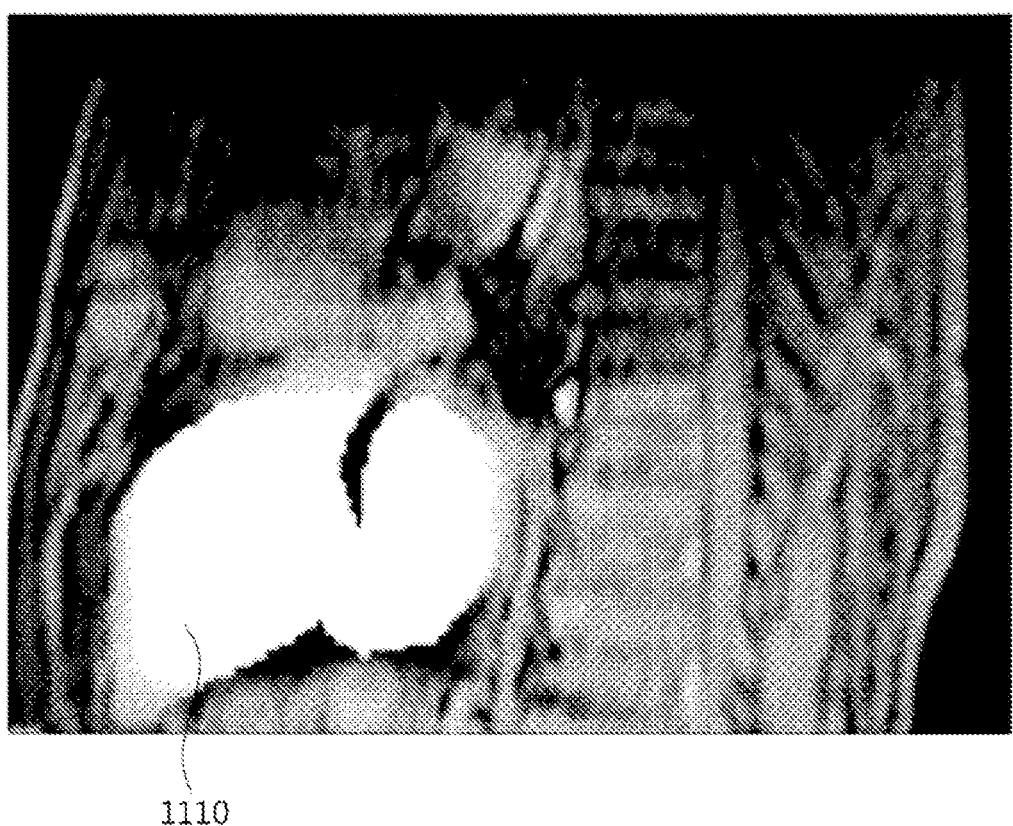
FIG. 7 is a diagram illustrating a case in which segmentation is performed on an extracted cross-sectional image, according to an exemplary embodiment.

FIG. 7 is a diagram illustrating a case in which segmentation is performed on an extracted cross-sectional image, according to an exemplary embodiment.

As illustrated in FIG. 7, a bright area represents a segmentation of a liver 1110 that is the anatomical object. Compared to anatomical objects other than the liver 1110, brightness and location information of the liver may be understood.

Figure 8:
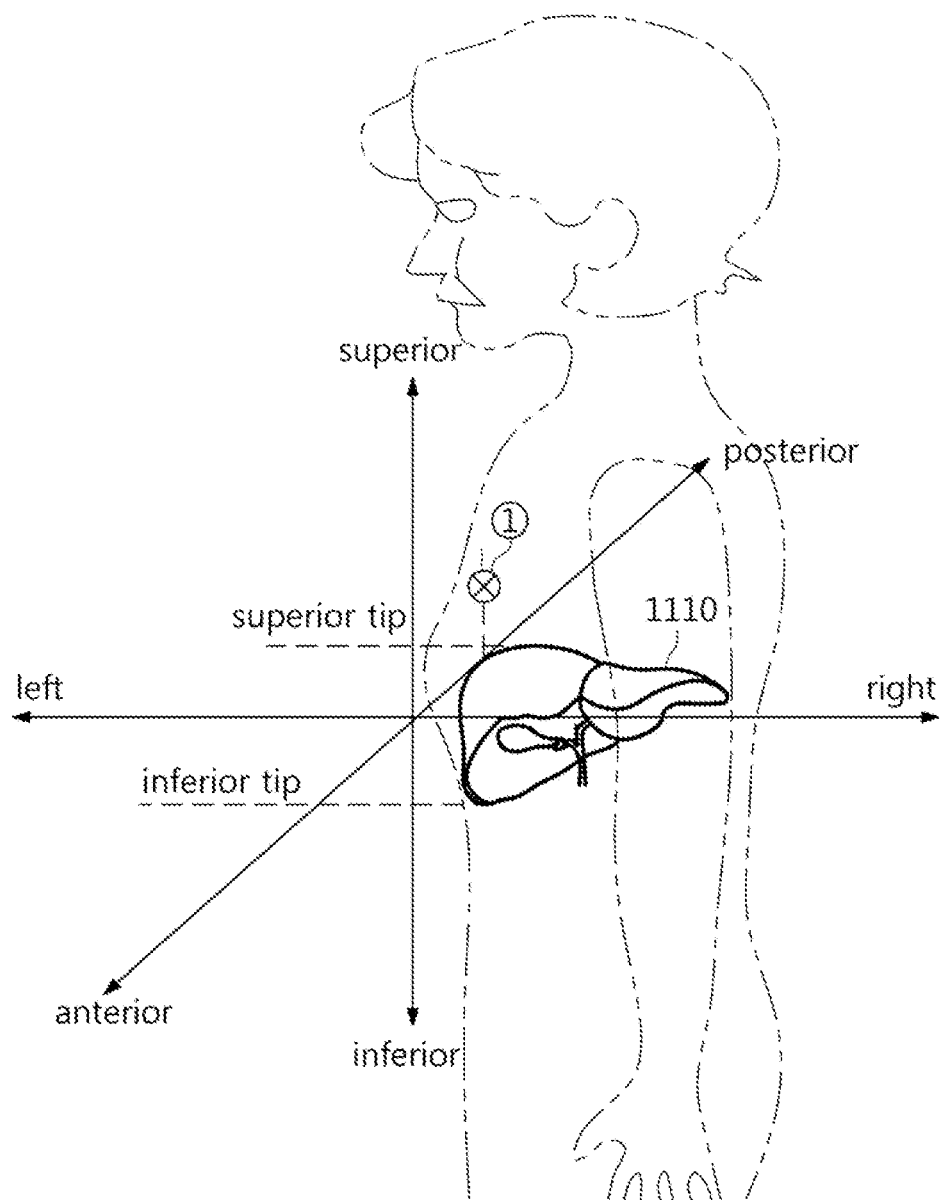
FIG. 8 illustrates assumed coordinate axes for extracting a location corresponding to the reference location of the probe placed on the object from the second medical image with respect to the liver that is the segmented anatomical object, according to the exemplary embodiment.

FIG. 8 illustrates assumed coordinate axes for extracting a location corresponding to the reference location of the probe placed on the object from the second medical image with respect to the liver that is the segmented anatomical object, according to the exemplary embodiment.

As illustrated in FIG. 8, the cross-sectional image in FIG. 7 is segmented, and then the corresponding location may be extracted from location information of the liver 1110.

Referring also to FIG. 4, in operation S140, the corresponding location extracting unit 230 may use an image in which anatomical objects shown in the cross-sectional image are segmented, and location information of an inside of the object is used to extract a location corresponding to the reference location of the probe 111 that is placed on the object. As illustrated in FIGS. 7 and 8, the segmented liver 1110 is the anatomical object of the body and has anatomical features such as location information and brightness information. As illustrated in FIG. 8, the location information of the liver 1110 may be represented in an anterior-posterior direction, a superior-inferior direction and a left-right direction. In this case, for convenience of description, when it is assumed in the present exemplary embodiment that location information of the liver 1110 in the superior-inferior direction is used, with respect to the middle sagittal plane, a point at which the top portion of the liver 1110 meets a superior axis may be represented as a superior-tip, and a point at which the bottom portion thereof meets an inferior axis may be represented as an inferior-tip. The superior-tip and the inferior-tip are located on the middle sagittal plane, and may be defined as different locations in another cross section. The inferior-tip or the superior-tip of the liver may also be clearly expressed in the ultrasound image, identified with the naked eye from the image, and a location of the liver 1110 may be identified in the MR image or the CT image by using the location information. Therefore, a location corresponding to the reference location of the probe 111 placed on the object may be found in the first medical image from location information of the liver 1110. This may be found by using coordinate information from the superior-tip or the inferior-tip of the liver 1110 to the solar plexus 12, or the superior-tip area may be directly set and used as a location of the solar plexus 12. However, a criterion of using location information is not limited thereto, and the corresponding location may be extracted in consideration of a location from the segmented anatomical objects.

As illustrated in FIG. 8, the corresponding location in the second medical image extracted by the corresponding location extracting unit 230 may be represented as ①.

Referring also to FIG. 4, in operation S150, the intersecting location extracting unit 240 may extract an intersecting location intersecting at the skin line 500 from the corresponding location extracted by the corresponding location extracting unit 230. When the first medical image is obtained from the probe 111, since the reference location of the probe 111 placed on the object corresponds to the skin line 500, in order to perform image registration using the reference location and the location extracted from the second medical image, the intersecting location at the skin line 500 should be extracted from a location of the solar plexus 12 extracted by the corresponding location extracting unit 230.

Figure 9:
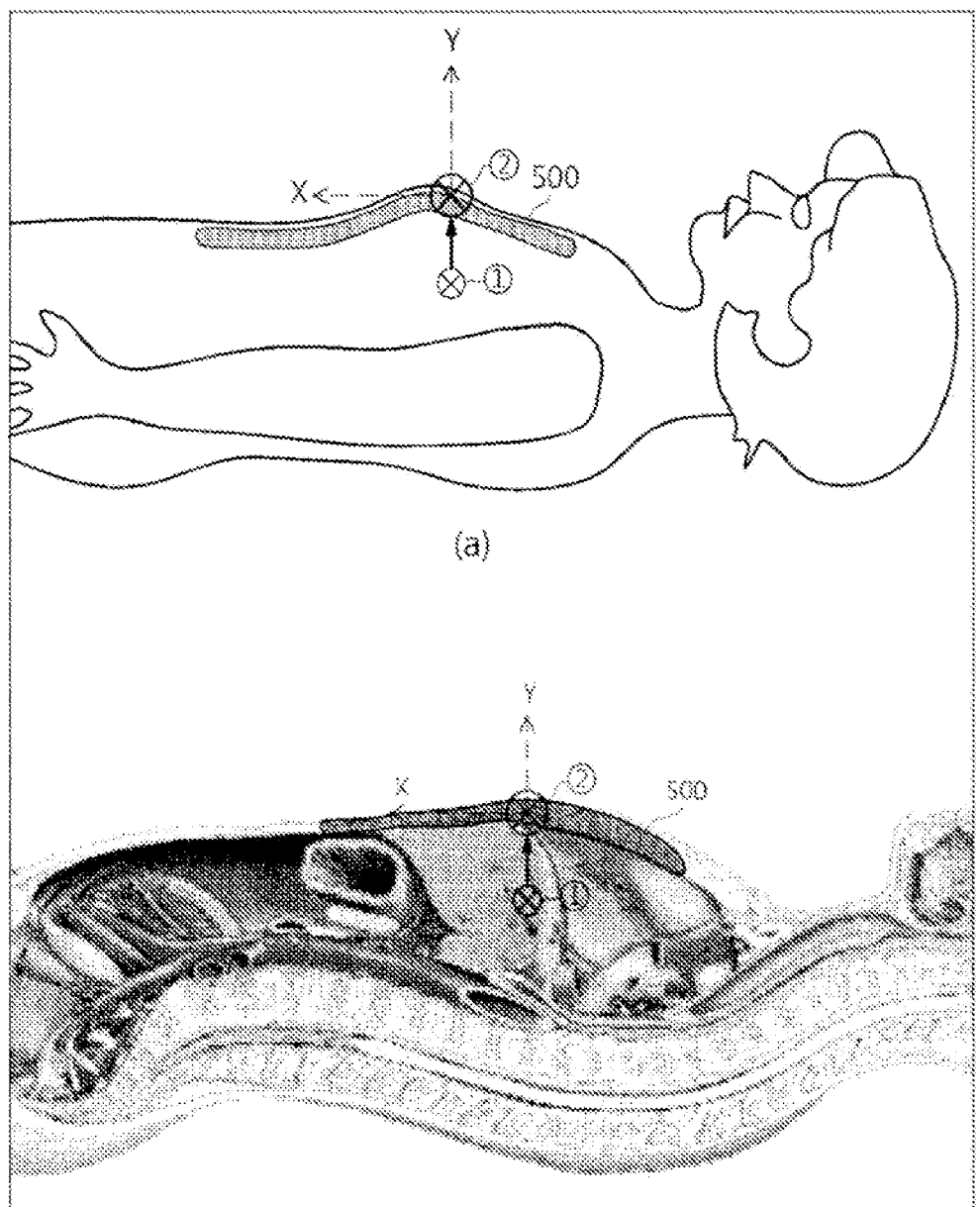
FIG. 9 is a diagram schematically illustrating a case in which a location intersecting at a skin line is extracted.

FIG. 9 is a diagram schematically illustrating a case in which a location intersecting at a skin line is extracted.

Drawing (a) on the left side of FIG. 9 represents an intersecting location when the object on which the probe 111 is placed is viewed from the outside. Drawing (b) on the right side of FIG. 9 represents a location intersecting at the skin line 500 in the cross-sectional image extracted from the second medical image. As illustrated in FIG. 9, ① represents the corresponding location extracted by the corresponding location extracting unit 230 and ② corresponds to the intersecting location at the skin line 500. As described above in FIG. 2, the user may place the probe 111 on the solar plexus 12. In this case, the axis 205 of the probe 111 may be set to be parallel with the axis 215 of the object. When the detecting device 130 is disposed on the reference location of the object and the axis of the probe 111 is parallel with the axis of the object, the detecting device 130 may calculate coordinate information of the probe 111. From the coordinate information and coordinate information of the corresponding location ① extracted by the corresponding location extracting unit 230 of the image processing apparatus 140, coordinate information of the intersecting location ② at the skin line 500 may be obtained.

A method of the intersecting location extracting unit 240 extracting the intersecting location ② will be described with reference to FIG. 9. First, the intersecting location may be found along an axis (i.e., a y-axis) reaching the skin line 500 from the corresponding location ①. When a direction of the skin line 500 of the object is set as an x-axis and a direction of the reference location in which the probe 111 is located and a direction in which the corresponding location ① approaches the intersecting location ② are set as a y-axis, a location at which the x-axis and the y-axis intersect at the skin line 500 may correspond to the intersecting location ② at the skin line 500. In a method of the intersecting location extracting unit 240 finding the skin line 500, since a difference between a brightness value in the skin and a brightness value in air varies in the MR image or the CT image, the skin line 500 may be found from data of the brightness value in the skin. Therefore, the skin line 500 is found, coordinate information of the probe 111 extracted by the detecting device 130 is applied to the corresponding location ①, an intersecting location at the skin line 500 in the y-axis direction is found, and then the intersecting location ② may be extracted.

Referring also to FIG. 4, in operation S160, the image registration unit 260 may perform image registration based on coordinate information of the reference location of the probe 111 placed on the object and coordinate information of the intersecting location at the skin line 500 extracted by the intersecting location extracting unit 240. The image registration unit 260 performs registration of the first medical image obtained from the first medical apparatus 110 with respect to the second medical image obtained from the second medical apparatus 120. Registration of the medical images may include an operation in which a coordinate system of the reference location of the probe 111 detected by the detecting device 130 and a coordinate system of the intersecting location extracted from the second medical image are mapped to each other. Movement of the probe 111 has a one-to-one correspondence with a view of the first medical image. The user more easily performs control of movement of the probe 111 than control of the first medical image. Therefore, when the image processing apparatus 140 according to the exemplary embodiment detects the reference location of the probe 111 and extracts the intersecting location of the second medical image corresponding to the reference location of the probe 111, different types of medical images may be registered with respect to each other. Since registration is performed based on the location extracted from the cross-sectional image of the second medical image, user convenience increases and a required time decreases.

In the exemplary embodiment, the registered image may be a fusion image in which the first medical image and the second medical image are fused. In another exemplary embodiment, the registered image may be an image in which the first medical image and the second medical image at the same observation viewpoint are disposed in parallel. Referring also to FIG. 4, in operation S170, the registered image may be displayed on the display unit 150.

Figure 10:
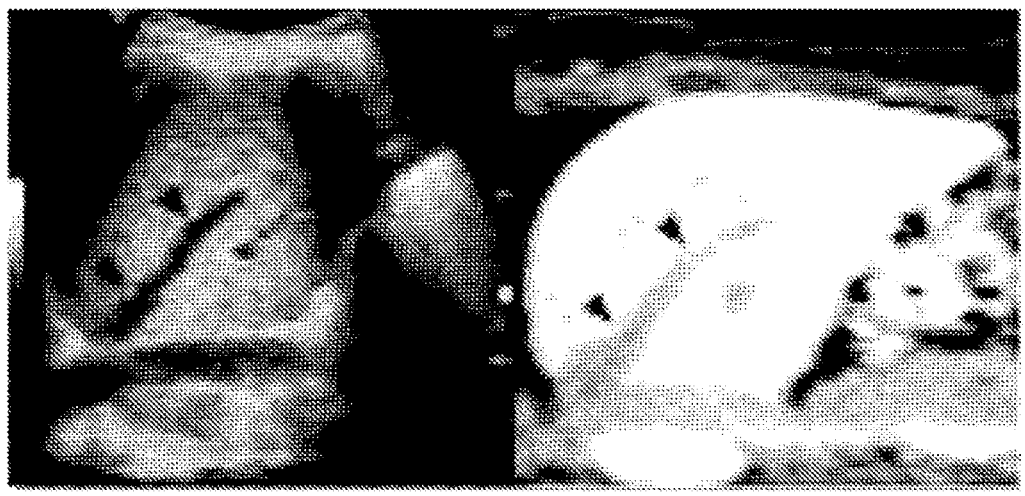
FIG. 10 shows an image in which a first medical image and a second medical image are registered and disposed in parallel when an object is a liver.

FIG. 10 shows an image in which a first medical image and a second medical image are registered and disposed in parallel when an object is a liver.

Drawing (a) on the left side of FIG. 10 represents an ultrasound image, and drawing (b) on the right side of FIG. 10 represents an MR image. The image is identified and observed in real time according to the same location and coordinates, and at the same time, it may be determined whether there is a lesion in the object.

Figure 11:
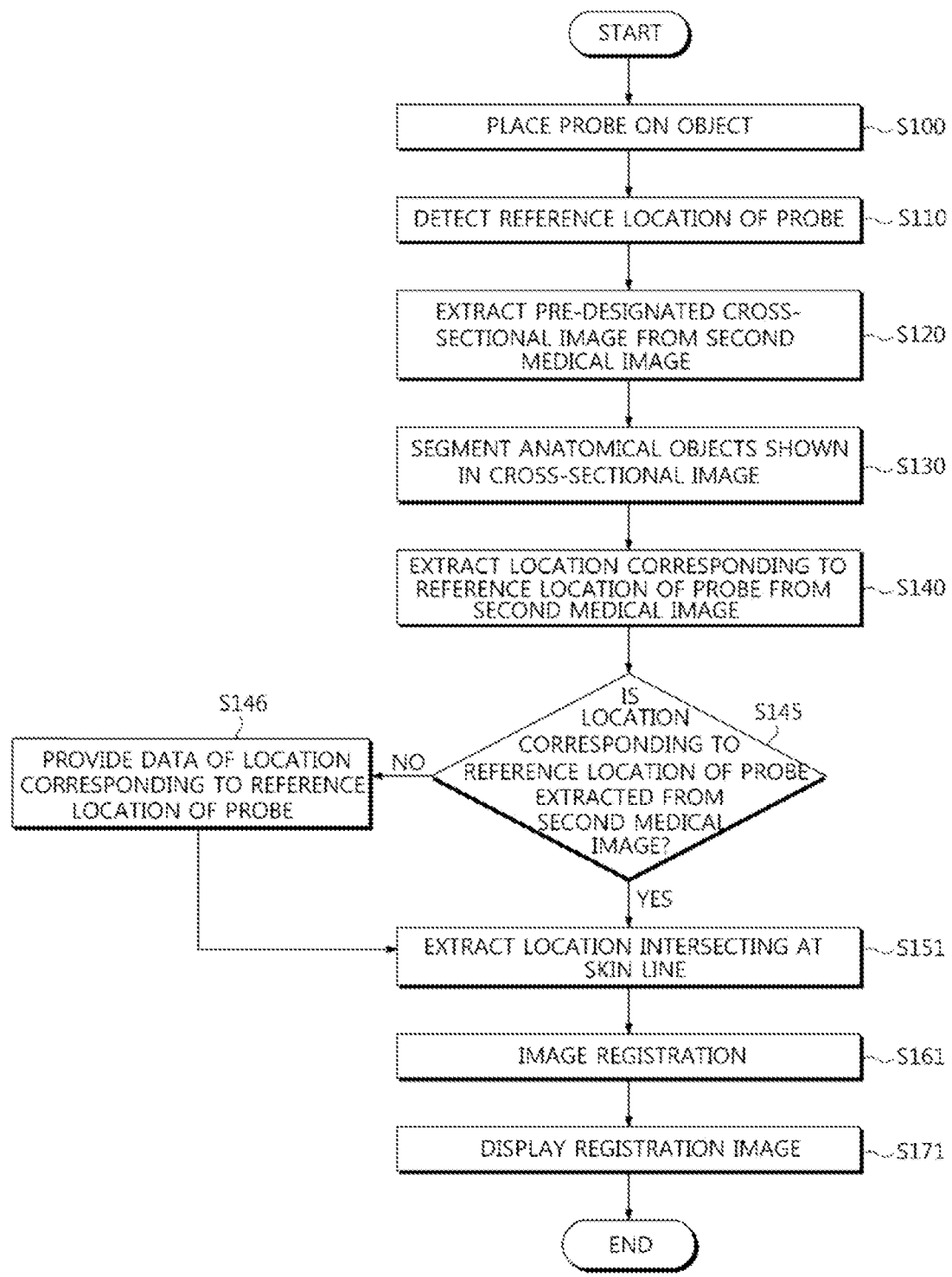
FIG. 11 is a flowchart illustrating an image processing method in which location data corresponding to a reference location of a probe is provided, according to an exemplary embodiment.

FIG. 11 is a flowchart illustrating an image processing method in which location data corresponding to a reference location of a probe is provided, according to an exemplary embodiment.

As illustrated in FIG. 11, the probe 111 is placed on the object in operation S100, the reference location of the probe 111 is detected in operation S110, a pre-designated cross-sectional image is extracted from the second medical image in operation S120, and anatomical objects shown in the extracted cross-sectional image are segmented in operation S130. Since the operation of extracting a location corresponding to the reference location of the probe 111 from the second medical image has been described in FIG. 4, redundant description thereof will be omitted.

When it is determined in the control unit 190 that a location corresponding to the reference location of the probe 111 is not extracted from the second medical image in operation S145, the corresponding location data providing unit 250 may provide data of the location corresponding to the reference location of the probe 111 in operation S146. The location corresponding to the reference location of the probe 111 may not be extracted when an error occurs in the extracting operation or when location information of segmented anatomical objects is unclear. The corresponding location data providing unit 250 may provide corresponding location data that is stored in the storage unit 180 in advance. The pre-stored data may be previously imaged medical images of other patients and location information obtained from information on other cross-sectional images. For example, from data of segmentation that is performed on the cross-sectional image of another object that has similar body information or anatomical information to the object of which the second medical image is imaged, corresponding location information of the area of the solar plexus 12 in which the probe 111 is located may be provided to set the corresponding location. In this case, since the corresponding location is not directly extracted from the cross section extracted from the second medical image, an error may occur when images are registered. As will be described below, when the location corresponding to the reference location of the probe 111 is additionally extracted from the second medical image, an error rate may be decreased.

When the corresponding location provided from the corresponding location data providing unit 250 is determined, as described above in FIG. 4, a location intersecting at the skin line is extracted using the corresponding location in operation S151, registration of the first medical image with respect to the second medical image is performed by using the extracted intersecting location in operation S161, and the registration image may be displayed in operation S171. In this case, since the respective operations of S151, S161, and S171 are similar to the corresponding operations of S150, S160, and S170 in FIG. 4 according to operations of that exemplary embodiment, the operations may be performed using the same method, although represented by different numerals.

Figure 12:
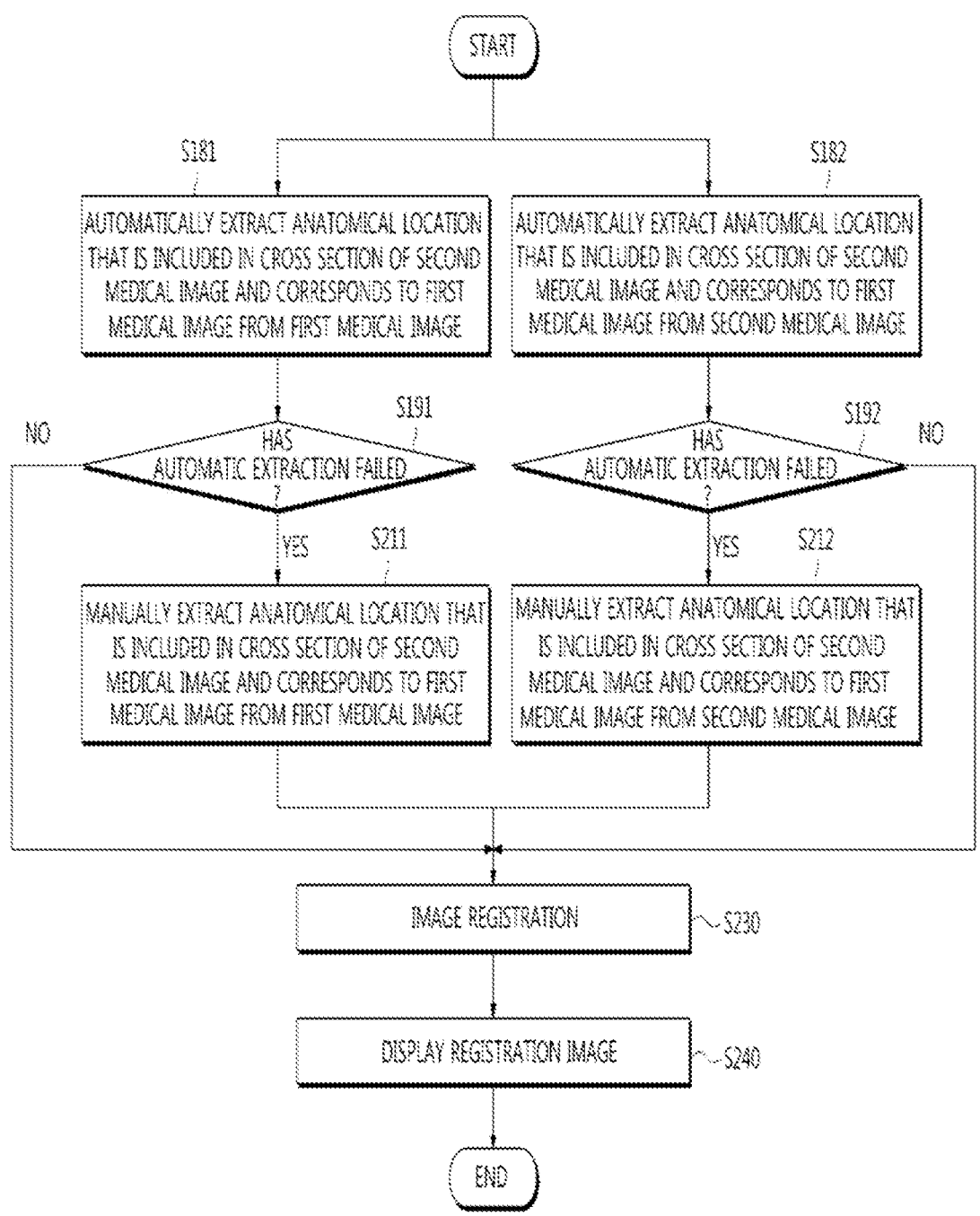
FIG. 12 is a flowchart illustrating an image processing method in which anatomical locations corresponding to a first medical image and a second medical image are additionally automatically extracted, and when automatic extraction has failed, manual extraction is performed, according to an exemplary embodiment.

FIG. 12 is a flowchart illustrating an image processing method in which anatomical locations corresponding to a first medical image and a second medical image are additionally automatically extracted, and when automatic extraction has failed, manual extraction is performed, according to an exemplary embodiment.

Before the embodiment in FIG. 12, operations of S100 to S170 in FIG. 4 are performed and then operations in FIG. 12 may start.

Before a start operation in FIG. 12, a series of operations of S100 to S170 for performing registration of the first medical image with respect to the second medical image and displaying the registered image are the same as those in FIG. 4. As a result of performing the operations in FIG. 12, although the respective operations of image registration (i.e., operation S230) and displaying the registration image (i.e., operation S240) and the corresponding operations of S160 and S170 in FIG. 4 are represented by different numerals because they belong to different exemplary embodiments, they may be performed using the same method.

First, after the registration image is displayed in operation S170, under control of the control unit 190, as a location included in the cross-sectional image extracted from the second medical image, the anatomically corresponding location extracting unit 270 may additionally automatically extract the anatomically corresponding location in the first medical image and the second medical image from the first medical image and the second medical image in operations S181 and S182. In this case, the anatomically corresponding location in the first medical image and the second medical image refers to a corresponding location in the registered first medical image and second medical image, and the anatomical location refers to a location included in the cross section of the second medical image. The anatomically corresponding location is additionally extracted so that an error rate decreases and registration is performed more accurately when the first medical image and the second medical image are registered.

In the described exemplary embodiment, when the middle sagittal plane is used as a reference, the anatomical location that is included in the middle sagittal plane that is a cross section extracted from the second medical image and corresponds in each of the first medical image and the second medical image may correspond to the inferior-tip described in FIG. 8. In particular, a location corresponding to the inferior-tip may be extracted from each of the first medical image and the second medical image and used for image registration. The above-described inferior-tip is located on the anatomical reference plane, but the exemplary embodiments are not limited thereto. When a cross section extracted from the second medical image is not the anatomical reference plane but is another cross section, another anatomical location that is included in the cross section of the second medical image and corresponds to the first medical image may be extracted. The anatomically corresponding location extracting unit 270 may automatically extract the anatomically corresponding location in the first medical image and the second medical image from each of the first medical image and the second medical image via image processing by using location information from the intersecting location that is extracted in the above operation S150 and used for image registration in operations S181 and S182.

In operations S191 and S192, the control unit 190 may determine whether the anatomically corresponding location is automatically extracted from each of the first medical image and the second medical image. The anatomical location is not automatically extracted when extraction has failed due to an error of image processing or when the liver serving as the segmented subject has an abnormal shape and it is difficult to extract the anatomical location such as the inferior-tip.

When the anatomically corresponding location is automatically extracted from each of the first medical image and the second medical image, in operation S230, the image registration unit 260 may perform image registration by using the extracted corresponding location.

When the anatomically corresponding location is not automatically extracted from the first medical image and the second medical image, in operations S211 and S212, the control unit 190 may manually extract the corresponding location. When the location is manually extracted, the user may input and set the location in the first medical image and the second medical image through the input unit 170.

According to the above operations, image registration may be performed by using the anatomically corresponding location extracted from the first medical image and the second medical image in operation S230, and the registered image may be displayed in operation S240. According to accuracy of registration, the above operations may be repeated.

Figure 13:
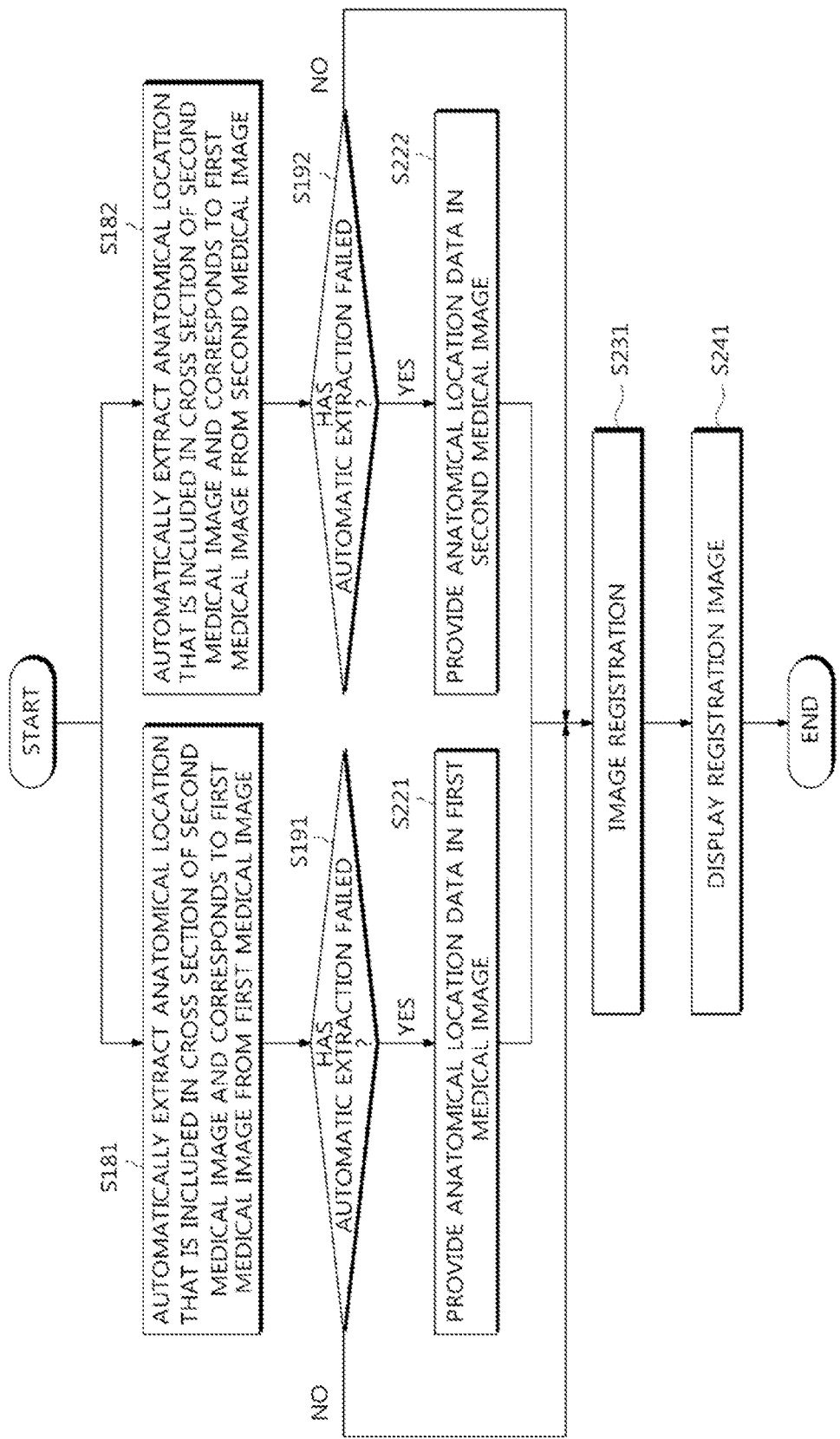
FIG. 13 is a flowchart illustrating an image processing method in which anatomical locations corresponding to a first medical image and a second medical image are additionally automatically extracted, and when automatic extraction has failed, anatomical location data is provided, according to an exemplary embodiment.

FIG. 13 is a flowchart illustrating an image processing method in which anatomical locations corresponding to a first medical image and a second medical image are additionally automatically extracted, and when automatic extraction has failed, anatomical location data is provided, according to an exemplary embodiment.

Before the exemplary embodiment in FIG. 13, operations of S100 to S170 in FIG. 4 are performed and then operations in FIG. 13 may start.

Before a start operation in FIG. 13, a series of operations of S100 to S170 for performing registration of the first medical image with respect to the second medical image an displaying the registered image are the same as those in FIG. 4. As a result of performing the operations in FIG. 13, although the respective operations of image registration (i.e., operation S231) and displaying the registration image (i.e., operation S241) and the corresponding operations of S160 and S170 in FIG. 4 are represented by different numerals because they belong to different exemplary embodiments, they may be performed using the same method.

Since operations before operations S191 and S192 of the control unit 190 determining whether the anatomically corresponding location is automatically extracted from the first medical image and the second medical image are the same as those in FIG. 12, redundant description thereof will be omitted.

When the anatomically corresponding location is not automatically extracted from the first medical image and the second medical image, the anatomical location data providing unit 280 may provide anatomical location data corresponding in the first medical image and the second medical image in operations S221 and S222. The anatomical location data providing unit 280 may provide the anatomically corresponding location in each of the first medical image and the second medical image to be used for image registration based on anatomical location data stored in the storage unit 180. For example, when the location is not automatically extracted, anatomical location data of the inferior-tip located on the middle sagittal plane may be provided.

According to the above operations, image registration may be performed by using the extracted or provided anatomically corresponding location from the first medical image and the second medical image in operation S231, and the registered image may be displayed in operation S241. According to accuracy of registration, the above operations may be repeated.

Figure 14:
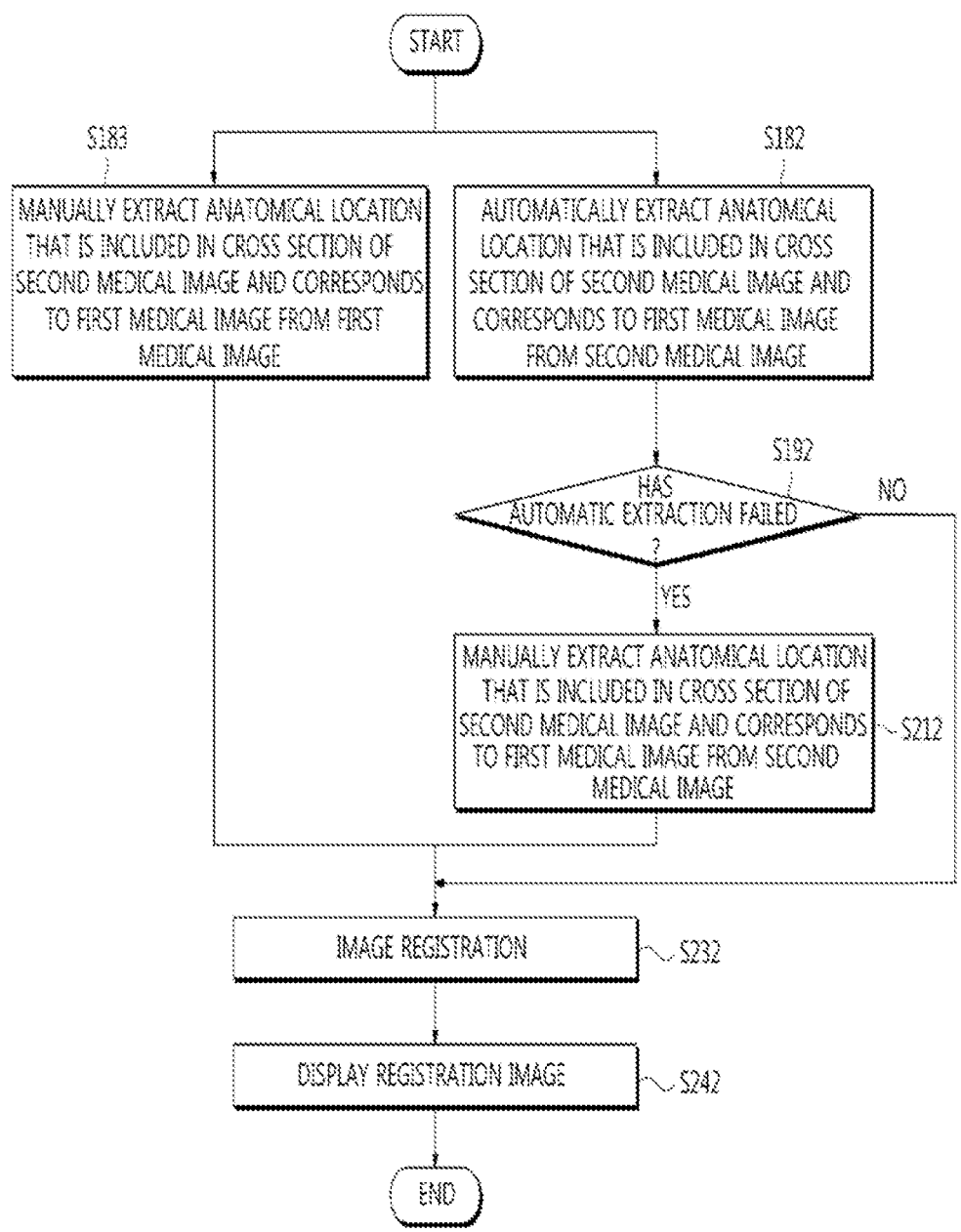
FIG. 14 is a flowchart illustrating an image processing method in which anatomical locations corresponding to a first medical image and a second medical image are manually extracted from the first medical image and automatically extracted from the second medical image, and when automatic extraction has failed in the second medical image, manual extraction is performed, according to an exemplary embodiment.

FIG. 14 is a flowchart illustrating an image processing method in which anatomical locations corresponding to a first medical image and a second medical image are manually extracted from the first medical image and automatically extracted from the second medical image, and when automatic extraction has failed in the second medical image, manual extraction is performed, according to an exemplary embodiment.

Before the embodiment in FIG. 14, operations of S100 to S170 in FIG. 4 are performed and then operations in FIG. 14 may start.

Before a start operation in FIG. 14, a series of operations of S100 to S170 for performing registration of the first medical image with respect to the second medical image and displaying the registered image are the same as those in FIG. 4. As a result of performing the operations in FIG. 14, although the respective operations of image registration (i.e., operation S232) and displaying the registration image (i.e., operation S242) and the corresponding operations of S160 and S170 in FIG. 4 are represented by different numerals because they belong to different exemplary embodiments, they may be performed using the same method.

First, after the registration image is displayed in operation S170, under control of the control unit 190, the anatomically corresponding location extracting unit 270 may additionally automatically extract the anatomically corresponding location in each of the first medical image and the second medical image from the second medical image in operation S182.

In addition, the anatomically corresponding location may be manually extracted from the first medical image in operation S183, and the user may input and set the location in the first medical image via the input unit 170.

When the location is manually extracted from the first medical image and automatically extracted from the second medical image, the image registration unit 260 may perform image registration by using the extracted corresponding location in operation S232.

The control unit 190 may determine whether the anatomically corresponding location is automatically extracted from the second medical image in operation S192. When the anatomically corresponding location is not automatically extracted from the second medical image, the control unit 190 may manually extract the corresponding location in operation S212. When the location is manually extracted, the user may input and set the location in the second medical image via the input unit 170.

According to the above operations, image registration may be performed using the anatomically corresponding location extracted from the first medical image and the second medical image (i.e., operation S232) and the registered image may be displayed (i.e., operation S242). According to accuracy of registration, the above operations may be repeated.

Figure 15:
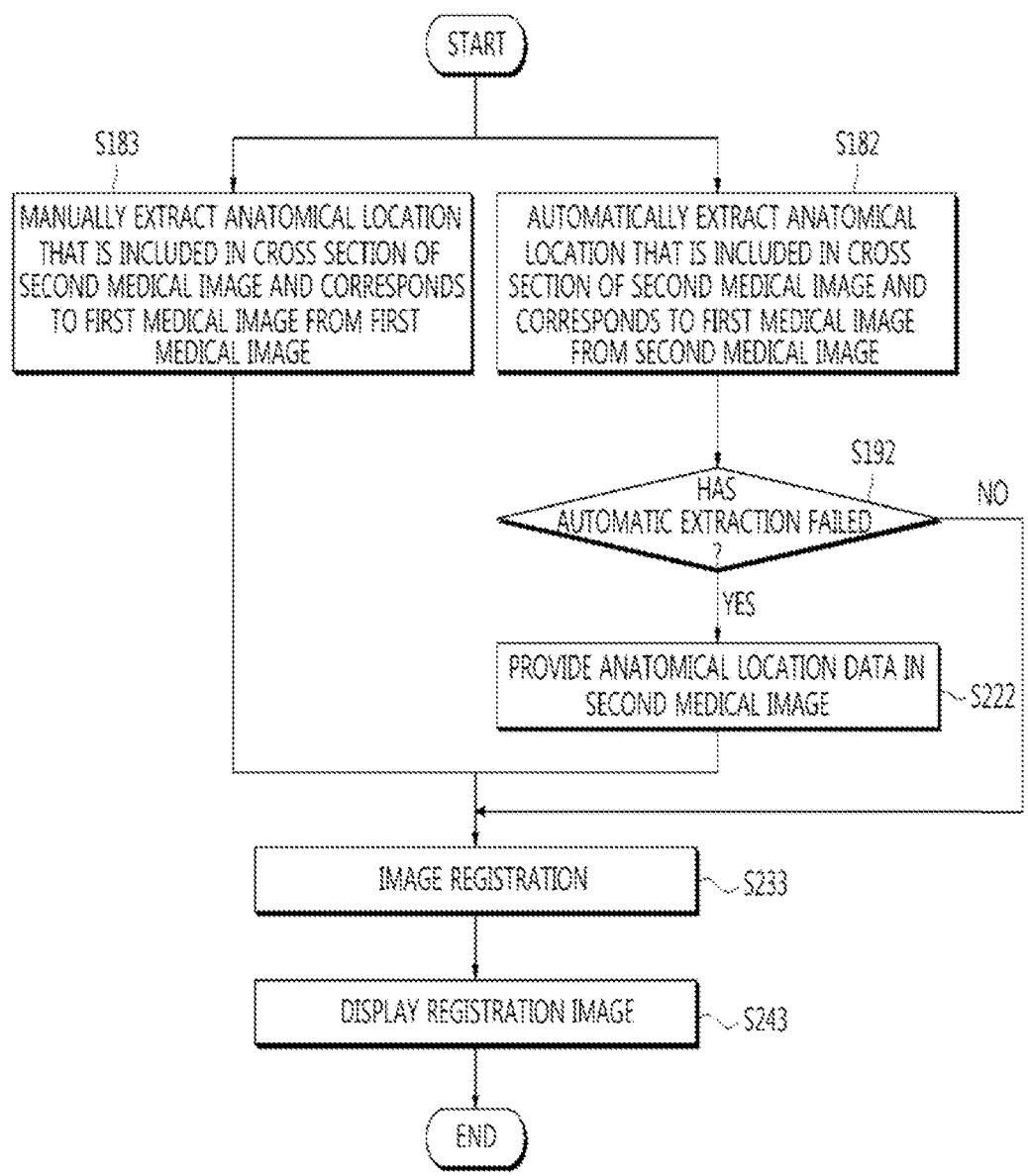
FIG. 15 is a flowchart illustrating an image processing method in which anatomical locations corresponding to a first medical image and a second medical image are manually extracted from the first medical image and automatically extracted from the second medical image, and when automatic extraction has failed in the second medical image, anatomical location data is provided, according to an exemplary embodiment.

FIG. 15 is a flowchart illustrating an image processing method in which anatomical locations corresponding to a first medical image and a second medical image are manually extracted from the first medical image and automatically extracted from the second medical image, and when automatic extraction has failed in the second medical image, anatomical location data is provided, according to an exemplary embodiment.

Before the exemplary embodiment in FIG. 15, operations of S100 to S170 in FIG. 4 and then operations in FIG. 15 may start.

Before a start operation in FIG. 15, a series of operations of S100 to S170 for performing registration of the first medical image and the second medical image and displaying the registered image are the same as those in FIG. 4. As a result of performing the operations in FIG. 15, although the respective operations of image registration (i.e., operation S233) and displaying the registration image (i.e., operation S243) and the corresponding operations of S160 and S170 in FIG. 4 are represented by different numerals because they belong to different exemplary embodiments, they may be performed using the same method.

First, after the registration image is displayed in operation S170, under control of the control unit 190, the anatomically corresponding location extracting unit 270 may additionally automatically extract the anatomically corresponding location in each of the first medical image and the second medical image from the second medical image in operation S182.

In addition, the anatomically corresponding location may be manually extracted from the first medical image in operation S183, and the user may input and set the location in the first medical image via the input unit 170.

When the anatomically corresponding location is manually extracted from the first medical image and automatically extracted from the second medical image, the image registration unit 260 may perform image registration by using the extracted corresponding location in operation S233.

The control unit 190 may determine whether the anatomically corresponding location is automatically extracted from the second medical image in operation S192. When the anatomically corresponding location is not automatically extracted from the second medical image, the anatomical location data providing unit 280 may provide the anatomical location data corresponding in the first medical image and the second medical image in operation S222.

According to the above operations, image registration may be performed by using the extracted or provided anatomically corresponding location from the first medical image and the second medical image in operation S233), and the registered image may be displayed in operation S243. According to accuracy of registration, the above operations may be repeated.

Figure 16:
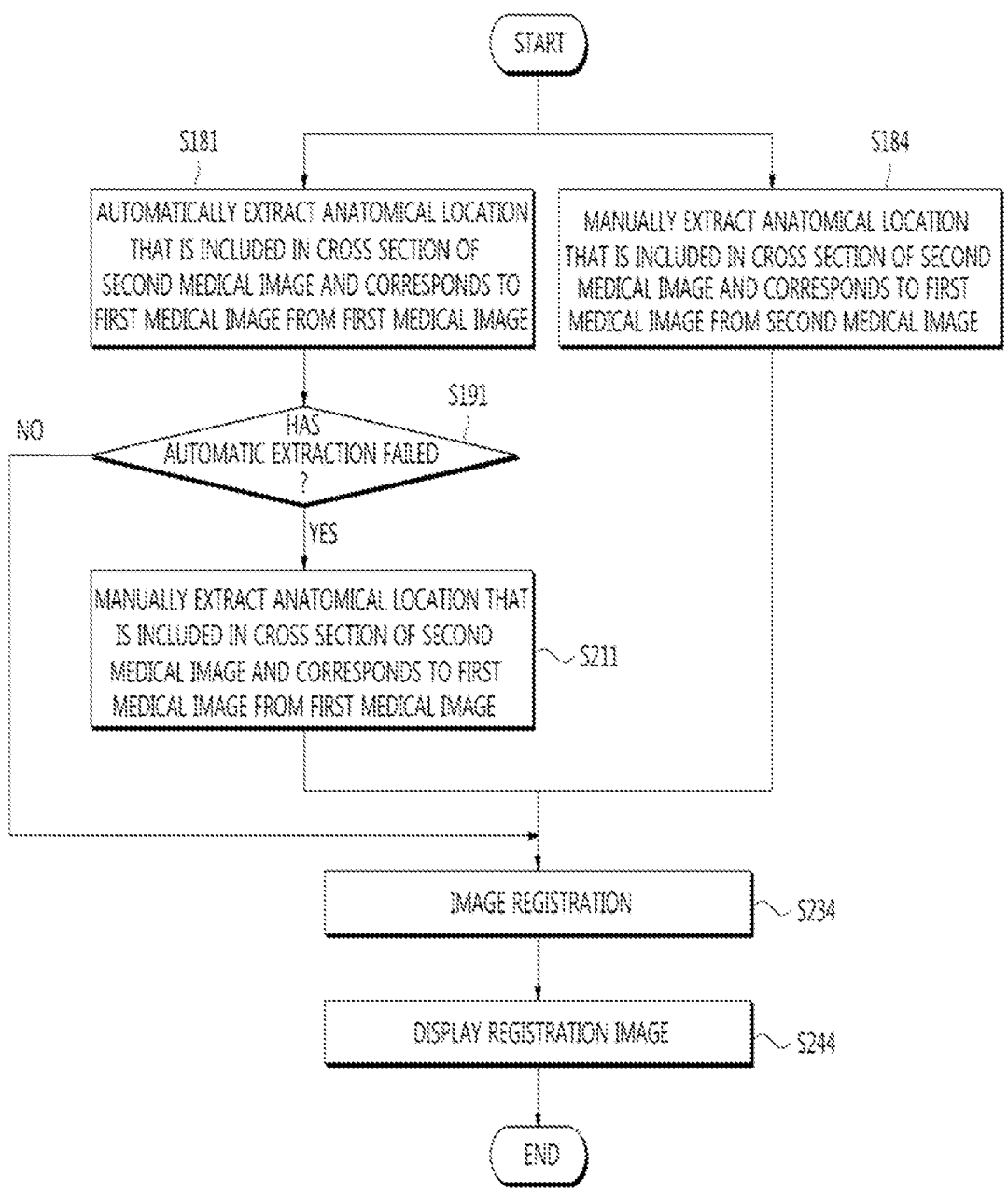
FIG. 16 is a flowchart illustrating an image processing method in which anatomical locations corresponding to a first medical image and a second medical image are automatically extracted from the first medical image and manually extracted from the second medical image, and when automatic extraction has failed in the first medical image, manual extraction is performed, according to an exemplary embodiment.

FIG. 16 is a flowchart illustrating an image processing method in which anatomical locations corresponding to a first medical image and a second medical image are automatically extracted from the first medical image and manually extracted from the second medical image, and when automatic extraction has failed in the first medical image, manual extraction is performed, according to an exemplary embodiment.

Before the exemplary embodiment in FIG. 16, operations of S100 to S170 in FIG. 4 and then operations in FIG. 14 may start.

Before a start operation in FIG. 16, a series of operations of S100 to S170 for performing registration of the first medical image and the second medical image and displaying the registered image are the same as those in FIG. 4. As a result of performing the operations in FIG. 16, although the respective operations of image registration (i.e., operation S234) and displaying the registration image (i.e., operation S244) and the corresponding operations of S160 and S170 in FIG. 4 are represented by different numerals because they belong to different exemplary embodiments, they may be performed using the same method.

First, after the registration image is displayed in operation S170, under control of the control unit 190, the anatomically corresponding location extracting unit 270 may additionally automatically extract the anatomically corresponding location in each of the first medical image and the second medical image from the first medical image in operation S181.

In addition, the anatomically corresponding location may be manually extracted from the second medical image in operation S184, and the user may input and set the location in the first medical image via the input unit 170.

When the anatomically corresponding location is automatically extracted from the first medical image and manually extracted from the second medical image, the image registration unit 260 may perform image registration by using the extracted corresponding location in operation S234.

The control unit 190 may determine whether the anatomically corresponding location is automatically extracted from the first medical image in operation S191. When the anatomically corresponding location is not automatically extracted from the first medical image, the control unit 190 may manually extract the corresponding location in operation S211. When the location is manually extracted, the user may input and set the location in the first medical image via the input unit 170.

According to the above operations, image registration may be performed by using the extracted anatomically corresponding location from the first medical image and the second medical image (i.e., operation S234) and the registered image may be displayed (i.e., operation S244). According to accuracy of registration, the above operations may be repeated.

Figure 17:
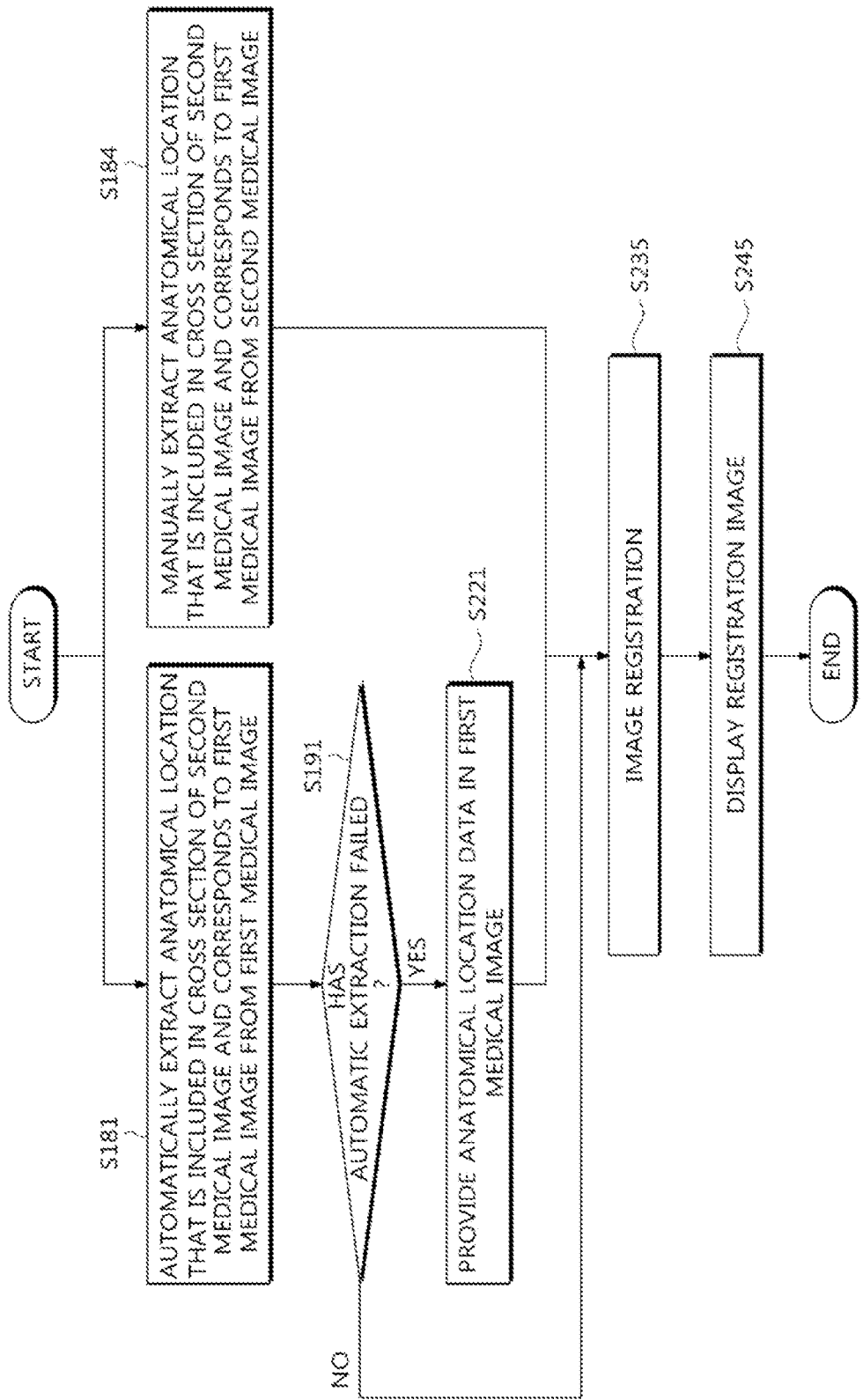
FIG. 17 is a flowchart illustrating an image processing method in which anatomical locations corresponding to a first medical image and a second medical image are automatically extracted from the first medical image and manually extracted from the second medical image, and when automatic extraction has failed in the first medical image, anatomical location data is provided, according to an exemplary embodiment.

FIG. 17 is a flowchart illustrating an image processing method in which anatomical locations corresponding to a first medical image and a second medical image are automatically extracted from the first medical image and manually extracted from the second medical image, and when automatic extraction has failed in the first medical image, anatomical location data is provided, according to an exemplary embodiment.

Before the exemplary embodiment in FIG. 17, operations of S100 to S170 in FIG. 4 are performed and then operations in FIG. 17 may start.

Before a start operation in FIG. 17, a series of operations of S100 to S170 for performing registration of the first medical image with respect to the second medical image and displaying the registered image are the same as those in FIG. 4. As a result of performing the operations in FIG. 17, although the respective operations of image registration (i.e., operation S235) and displaying the registration image (i.e., operation S245) and the corresponding operations of S160 and S170 in FIG. 4 are represented by different numerals because they belong to different exemplary embodiments, they may be performed using the same method.

First, after the registration image is displayed in operation S170, under control of the control unit 190, the anatomically corresponding location extracting unit 270 may additionally automatically extract the anatomically corresponding location in each of the first medical image and the second medical image from the first medical image in operation S181.

In addition, the anatomically corresponding location may be manually extracted from the second medical image in operation S184, and the user may input and set the location in the first medical image via the input unit 170.

When the anatomically corresponding location is automatically extracted from the first medical image and manually extracted from the second medical image, the image registration unit 260 may perform image registration using the extracted corresponding location in operation S235.

The control unit 190 may determine whether the anatomically corresponding location is automatically extracted from the first medical image in operation S191. When the anatomically corresponding location is not automatically extracted from the first medical image, the anatomical location data providing unit 280 may provide anatomical location data corresponding in the first medical image and the second medical image in operation S221.

According to the above operations, image registration may be performed using the extracted or provided anatomically corresponding location from the first medical image and the second medical image (i.e. operation S235), and the registered image may be displayed (i.e., operation S245). According to accuracy of registration, the above operations may be repeated.

Figure 18:
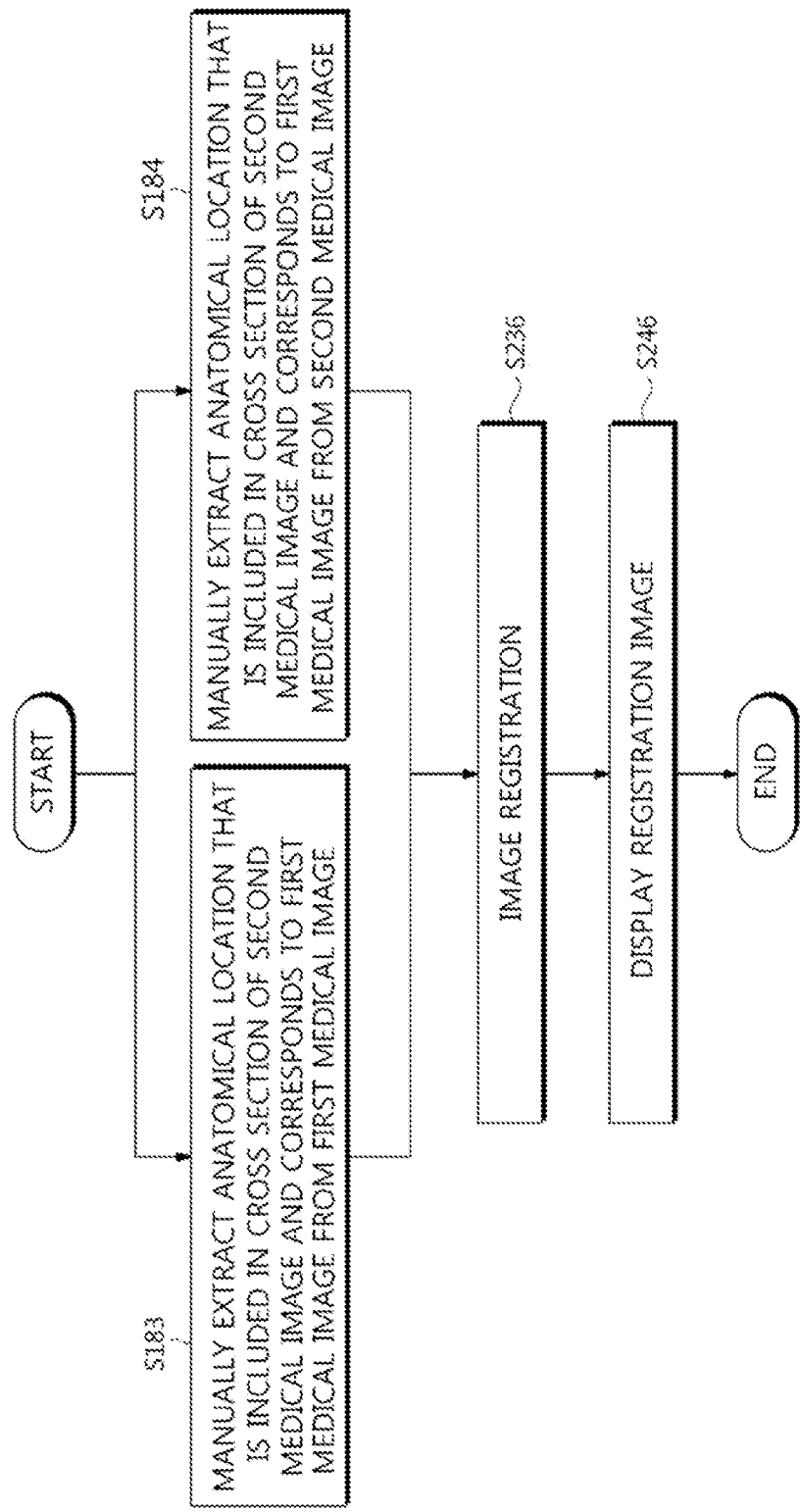
FIG. 18 is a flowchart illustrating an image processing method in which anatomical locations corresponding to a first medical image and a second medical image are additionally manually extracted, according to an exemplary embodiment.

FIG. 18 is a flowchart illustrating an image processing method in which anatomical locations corresponding to a first medical image and a second medical image are additionally manually extracted, according to an exemplary embodiment.

Before the exemplary embodiment in FIG. 18, operations of S100 to S170 in FIG. 4 are performed and then operations in FIG. 18 may start.

Before a start operation in FIG. 18, a series of operations of S100 to S170 for performing registration of the first medical image with respect to the second medical image and displaying the registered image are the same as those in FIG. 4. As a result of performing the operations in FIG. 18, although the respective operations of image registration (i.e., operation S236) and displaying the registration image (i.e., operation S246) and the operations of S160 and S170 in FIG. 4 are represented by different numerals because they belong to different exemplary embodiments, they may be performed using the same method.

The user may manually extract the anatomically corresponding location from the first medical image and the second medical image in operations S183 and S184. The user may input and set the location in the first medical image and the second medical image via the input unit 170.

When the anatomically corresponding location is manually extracted from each of the first medical image and the second medical image, the image registration unit 260 may perform image registration using the extracted corresponding location in operation S236, and the registered image may be displayed in operation S246.

According to another exemplary embodiment, after the operations in FIGS. 12 to 18 are performed, under control of the control unit 190, another anatomically corresponding location in the first medical image and the second medical image may be extracted from each of the first medical image and the second medical image. The anatomically corresponding location does not necessarily have to be the location included in the cross section of the second medical image described in FIGS. 12 to 18, but may be a point in any cross section or any location. Any anatomical location is additionally extracted so that image registration is performed more accurately. The extracting method may include automatic extraction and/or manual extraction. When manual extraction is performed, the user may input any anatomically corresponding location in the first medical image and the second medical image via the input unit 170 and extract the location from the first medical image and the second medical image.

Figure 19:
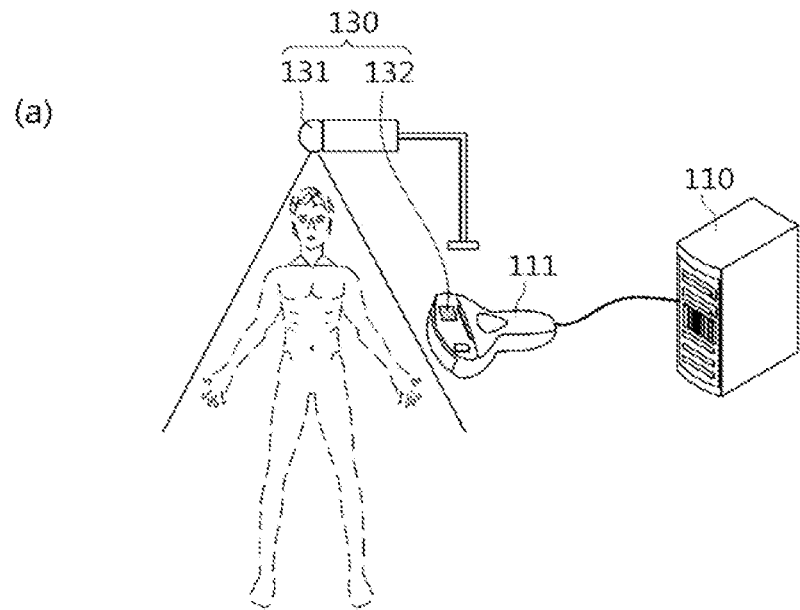
FIG. 19 is a perspective view of a medical imaging apparatus having an image processing unit, according to an exemplary embodiment.
Figure 19:
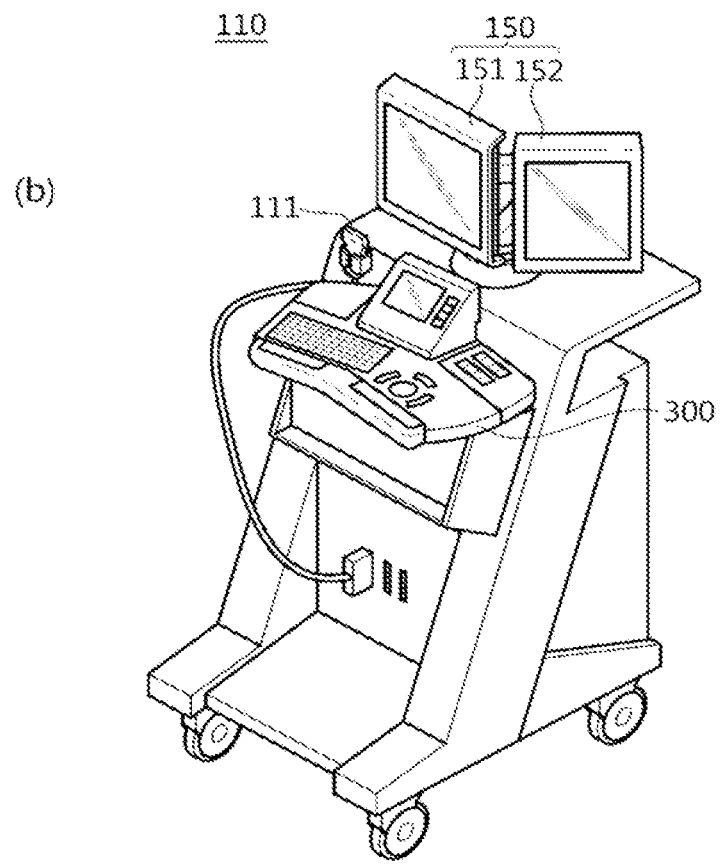

FIG. 19 is a perspective view of a medical imaging apparatus having an image processing unit, according to an exemplary embodiment.

Drawing (a) at the top of FIG. 19 illustrates a medical image processing system in which, in the image processing system 100 in FIG. 1, a first medical apparatus 110 corresponds to the ultrasound imaging apparatus 110 having the image processing unit 200 and serves as the image processing apparatus 140. Drawing (b) at the bottom of FIG. 19 illustrates the ultrasound imaging apparatus 110 corresponding to the first medical apparatus.

As illustrated in drawing (a) of FIG. 19, the first medical apparatus 110 obtains the first medical image of the object, receives the second medical image obtained from the second medical apparatus 120, and may perform image registration according to an exemplary embodiment. Since the detecting device 130 has been described above as illustrated in FIG. 1, redundant description thereof will be omitted.

As illustrated in drawing (b) of FIG. 19, the ultrasound probe 111 is a unit that comes in contact with a body surface of the object and may transmit and receive ultrasound energy to and from the object. Specifically, the ultrasound probe 111 generates ultrasound energy according to an input pulse, transmits the ultrasound energy into the object, and receives an echo ultrasound signal reflected from a specific area inside the object.

A manipulation panel 300 is a unit that is capable of receiving a command related to an operation of the ultrasound imaging apparatus 110. The user may input a command for performing a command for performing any of a diagnosis start, a diagnosis area selection, a diagnosis type selection, and/or a mode selection of an ultrasound image to be finally output via the manipulation panel 300. In addition, the manipulation panel 300 may receive an input for manipulating the image processing apparatus 140 from the user, similar to the input unit 170 in FIG. 3, and may receive an input for manually extracting the anatomically corresponding location in each of the first medical image and the second medical image from the first medical image and the second medical image. In this aspect, an input for the exemplary embodiment may be received. Exemplary modes of the ultrasound image may include an amplitude mode (A-mode), a brightness mode (B-mode), a Doppler mode (D-mode), an elastography mode (E-mode) and a motion mode (M-mode). As an exemplary embodiment, the manipulation panel 300 may be located above the main body and may include at least one of a switch, a key, a wheel, a joystick, a trackball and a knob.

The display unit 150 may display ultrasound images obtained in an ultrasound diagnostic process. The display unit 150 may be coupled to and mounted on the main body as illustrated in FIG. 19, or may be implemented to be detachable from the main body.

In addition, the display unit 150 may include a plurality of display devices 151 and 152 and display different images at the same time. For example, the first display device 151 may display an ultrasound image that is obtained by imaging the object, and the second display device 152 may display a registration image. The first display device 151 may display a 2D image that is obtained by imaging the object and the second display device 152 may display a 3D image.

In addition, each of the display devices 151 and 152 may include a display panel such as any of a plasma display panel (PDP), a liquid crystal display (LCD) panel, a light emitting diode (LED) panel, an organic light emitting diode (OLED) panel, and/or an active-matrix organic light-emitting diode (AMOLED) panel.

It is possible to obtain an ultrasound image of the object using the above ultrasound imaging apparatus 110.

Figure 20:
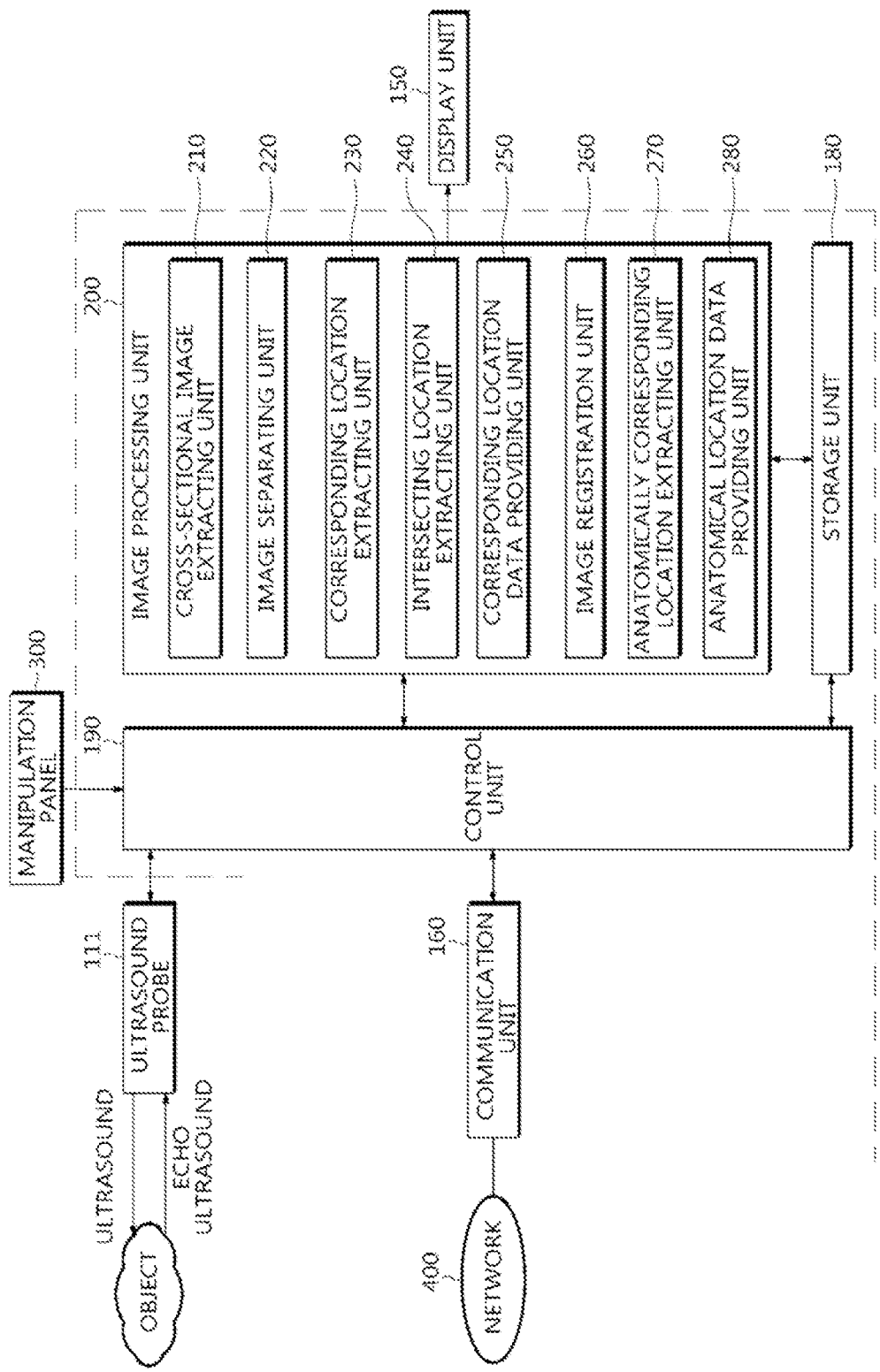
FIG. 20 is a control block diagram of a medical imaging apparatus, according to an exemplary embodiment.

FIG. 20 is a control block diagram of a medical imaging apparatus, according to an exemplary embodiment.

The image processing apparatus 140 may be implemented as a separate apparatus including software as illustrated in FIG. 3 or implemented as the image processing unit 200 in the ultrasound imaging apparatus 110 as illustrated in FIG. 20.

As illustrated in FIG. 20, the ultrasound imaging apparatus 110 according to the exemplary embodiment may include the communication unit 160, the storage unit 180, the control unit 190 and the image processing unit 200.

According to the exemplary embodiment, when the first medical apparatus 110 is the ultrasound imaging apparatus, the ultrasound imaging apparatus 110 radiates ultrasound energy onto the object and detects a reflected ultrasound signal by using the ultrasound probe 111, and therefore generates an ultrasound image.

The communication unit 160 may receive the first medical image and the second medical image from the first medical apparatus 110 and the second medical apparatus 120, respectively, and receive at least one of location information and direction information of the probe 111 from the detecting device 130. In particular, the communication unit 160 may be connected to other apparatuses connected to a network 400 and receive image data of the object imaged as the MR image or the CT image.

Functions and operations of components illustrated in FIG. 20 are the same as those in the above-described image processing apparatus 140 and the same as those in the control block diagram in FIG. 3. However, when the first medical apparatus 110 is the ultrasound imaging apparatus 110, the ultrasound imaging apparatus 110 has the image processing unit 200 and implements the exemplary embodiment similarly as described above, and redundant description thereof will be omitted.

When one of a plurality of medical images is a cross-sectional image, there is no need to obtain a 3D volume image. Automatic registration may be quickly and conveniently performed by using a cross section in the 3D volume image. As a result, user convenience increases and a required time decreases.

Exemplary embodiments of the image processing apparatus and the method for controlling the same have been described above with reference to the exemplified drawings. Examples of the image processing apparatus and the method of controlling the same are not limited thereto, and the exemplary embodiments described above are only examples in all aspects. Therefore, it will be understood by those of skill in the art that the exemplary embodiments may be performed in other concrete forms without changing the technological scope and essential features. Therefore, the scope of the present inventive concept is defined not by the detailed description but by the appended claims. All modifications and equivalents that fall within the scope of the appended claims will be construed as being included in the present inventive concept.

What is claimed is:

1. An image processing apparatus, comprising:
a transceiver configured to receive a first medical image of an object from a first medical apparatus, and to receive a second medical image of the object from a second medical apparatus; and
an image processor configured to extract a pre-designated cross-sectional image from the second medical image, to attempt to perform an automatic extraction to extract a corresponding location that corresponds to a reference location of the object from the extracted cross-sectional image, to detect a failure of the automatic extraction, and to perform a manual extraction to extract the corresponding location based on the detecting of the failure,
wherein the corresponding location is different from the reference location,
wherein the reference location refers to a location of a navigator placed on the object, the navigator including at least one from among an optical tracker and a procedure tool in which a sensor configured for navigating a location is mounted,
wherein the image processor is further configured to perform image processing which relates to at least one anatomical object shown in the extracted cross-sectional image and to extract an anatomical object location different from the reference location,
wherein the image processor is further configured to:
determine a skin line based on a brightness value,
determine a direction of the skin line as a horizontal axis,
determine coordinate information of the navigator,
determine a direction approaching the skin line from the corresponding location as a vertical axis,
determine an intersection of the horizontal axis and the vertical axis as an intersecting location based on the skin line and the coordinate information of the navigator, and
perform a registration of the second medical image with respect to the first medical image based on the corresponding location, the intersecting location, and the anatomical object location, when the navigator is disposed on the reference location of the object and an axis of the navigator is parallel with an axis of the object,
wherein the corresponding location is located inside of the object,
wherein the corresponding location is different from the intersecting location,
wherein the image processor is further configured to extract an anatomically corresponding location in each of the first medical image and the second medical image, and
wherein the manual extraction is performed based on a user input specifying the corresponding location.

2. The image processing apparatus according to claim 1, wherein the first medical image includes at least one from among an ultrasound image, an optical coherence tomography (OCT) image, a computed tomography (CT) image, an magnetic resonance (MR) image, an X-ray image, a single photon emission computed tomography (SPECT) image, a positron emission tomography (PET) image, a PET-CT image, fluoroscopy image, and a C-arm image, and
wherein the second medical image includes at least one from among an ultrasound image, an OCT image, a CT image, an MR image, an SPECT image, a PET image, PET-CT image, fluoroscopy image, X-ray image and a C-arm image.

3. The image processing apparatus according to claim 1, wherein the intersecting location is an intersecting point in an axial direction in which the navigator is located with respect to the anatomical object location.

4. The image processing apparatus according to claim 1, wherein the image processor is further configured to provide location data that corresponds to the reference location of the navigator in the extracted cross-sectional image.

5. The image processing apparatus according to claim 1, wherein the anatomically corresponding location in each of the first medical image and the second medical image corresponds to a location included in the cross-sectional image extracted from the second medical image.

6. The image processing apparatus according to claim 1, wherein the image processor is further configured to provide anatomically corresponding location data in each of the first medical image and the second medical image.

7. The image processing apparatus according to claim 1, further comprising
a display configured to display a registered image by using the reference location of the object or the intersecting location that intersects at a skin line.

8. The image processing apparatus of claim 1, wherein the image processor is further configured to perform segmentation with respect to the era cross-sectional image by using one from among a graph cut technique and a Gaussian model technique to obtain separate images of the object.

9. The image processing apparatus of claim 1, wherein the intersecting location is located within a boundary defined by the skin line.

10. The image processing apparatus of claim 1, wherein a horizontal coordinate of the corresponding location in a horizontal direction is equal to a horizontal coordinate of the reference location in the horizontal direction.

11. The image processing apparatus of claim 1, wherein the vertical axis approaches the skin line through the object from the corresponding location.

12. A method for controlling an image processing apparatus, comprising:
receiving, from a first medical apparatus, a first medical image of an object, and receiving, from a second medical apparatus, a second medical image of the object;
extracting a pre-designated cross-sectional image from the second medical image;
performing image processing of an anatomical object shown in the extracted cross-sectional image to extract an anatomical object location different from a reference location;
attempting to perform an automatic extraction to extract a corresponding location that corresponds to the reference location of the object;
detecting a failure of the automatic extraction,
based on the detecting of the failure, perform a manual extraction to extract the corresponding location;
determining a skin line based on a brightness value,
determining a direction of the skin line as a horizontal axis,
determining coordinate information of a navigator,
determining a direction approaching the skin line from the corresponding location as a vertical axis, determining an intersection of the horizontal axis and the vertical axis as an intersecting location based on the skin line and the coordinate information of the navigator, performing a registration of the second medical image with respect to the first medical image based on the corresponding location, the intersecting location, and the anatomical object location when the navigator is disposed on the reference location of the object and an axis of the navigator is parallel with an axis of the object, and extracting an anatomically corresponding location in each of the first medical image and the second medical image, wherein the corresponding location is different from the reference location, wherein the reference location refers to a location of the navigator placed on the object, the navigator including at least one from among an optical tracker and a procedure tool in which a sensor configured for navigating a location is mounted, wherein the corresponding location is located inside of the object, wherein the corresponding location is different from the intersecting location, and wherein the manual extraction is performed based on a user input specifying the corresponding location.

13. The method according to claim 12, further comprising providing location data that corresponds to the reference location of the navigator in the extracted cross-sectional image.

14. The method according to claim 12,
further comprising extracting anatomically corresponding location data in each of the first medical image and the second medical image.

15. A medical imaging apparatus, comprising:
a probe configured to obtain a first medical image of an object; and
an image processor configured to extract a pre-designated cross-sectional image from a second medical image that has a different modality from the first medical image, to attempt to perform an automatic extraction to extract a corresponding location that corresponds to a reference location of the object from the extracted cross-sectional image to detect a failure of the automatic extraction, and to perform a manual extraction to extract the corresponding location based on the detecting of the failure, wherein the corresponding location is different from the reference location, wherein the reference location refers to a location of a navigator placed on the object, the navigator including at least one from among an optical tracker and a procedure tool in which a sensor configured for navigating a location is mounted, wherein the image processor is further configured to:
perform image processing of an anatomical object shown in the extracted cross-sectional image to extract an anatomical object location different from the reference location;

determine a skin line based on a brightness value determine a direction of the skin line as a horizontal axis;

determine coordinate information of the navigator, determine a direction approaching the skin line from the corresponding location as a vertical axis; and determine an intersection of the horizontal axis and the vertical axis as an intersecting location based on the skin line and the coordinate information of the navigator; and perform a registration of the second medical image with respect to the first medical image based on the corresponding location, the intersecting location, and the anatomical object location when the navigator is disposed on the reference location of the object and an axis of the navigator is parallel with an axis of the object, wherein the corresponding location is located inside of the object, wherein the corresponding location is different from the intersecting location, wherein the image processor is further configured to extract an anatomically corresponding location in each of the first medical image and the second medical image, and wherein the manual extraction is performed based on a user input specifying the corresponding location.

16. The medical imaging apparatus according to claim 15, wherein the sensor is further configured to detect coordinate information that relates to a location and a direction of the probe with respect to the object.

17. The medical imaging apparatus of claim 15, wherein the image processor is further configured to extract the cross-sectional image from the second medical image based on statistical location information of the object.

* * * * *